US012089973B2

United States Patent
Henniges et al.

(10) Patent No.: US 12,089,973 B2
(45) Date of Patent: Sep. 17, 2024

(54) METAL DETECTION SYSTEM FOR USE WITH MEDICAL WASTE CONTAINER

(71) Applicant: Stryker Corporation, Kalamazoo, MI (US)

(72) Inventors: Bruce D. Henniges, Galesburg, MI (US); Christopher Philipp, Portage, MI (US); Andrew Lee Wallner, Grand Rapids, MI (US); Erik Vaclav Chmelar, Midland, MI (US); Jeffrey Lee Vanoss, Grand Rapids, MI (US)

(73) Assignee: Stryker Corporation, Kalamazoo, MI (US)

( * ) Notice: Subject to any disclaimer, the term of this patent is extended or adjusted under 35 U.S.C. 154(b) by 105 days.

(21) Appl. No.: 17/888,678

(22) Filed: Aug. 16, 2022

(65) Prior Publication Data
US 2022/0395347 A1    Dec. 15, 2022

Related U.S. Application Data

(63) Continuation of application No. 17/314,463, filed on May 7, 2021, now Pat. No. 11,446,109, which is a
(Continued)

(51) Int. Cl.
*A61B 50/36*    (2016.01)
*A61B 50/13*    (2016.01)
(Continued)

(52) U.S. Cl.
CPC .............. *A61B 50/36* (2016.02); *A61B 50/13* (2016.02); *A61B 50/30* (2016.02);
(Continued)

(58) Field of Classification Search
CPC ......... A61B 50/36; A61B 50/13; A61B 50/30; A61B 50/3001; B09B 3/00; B09B 3/0075; B65F 1/1415; G01N 27/023; G01V 3/104
(Continued)

(56) References Cited

U.S. PATENT DOCUMENTS 4,024,468 A    5/1977    Hirschi
4,464,622 A    8/1984    Franklin
(Continued)

FOREIGN PATENT DOCUMENTS

JP    S58171690 A    10/1983
JP    859024282 A    2/1984
(Continued)

OTHER PUBLICATIONS

US 11,413,108 B2, 08/2022, Henniges et al. (withdrawn)
(Continued)

*Primary Examiner* — Kerri L McNally
(74) *Attorney, Agent, or Firm* — Howard & Howard Attorneys PLLC

(57) ABSTRACT

A system for detecting disposal of metallic objects into an opening of a medical waste container, including: an indicator for indicating passage of metallic objects through the opening, a pair of receive coils and a transmit coil spaced therebetween shaped for receiving waste therethrough adjacent to the opening, and a controller in electrical communication with the coils. The controller generates and communicates a transmit signal to the transmit coil, which generates a magnetic field that induces voltage in each of the receive coils, which each generate a receive signal. The controller generates a waveform based on the receive signals with a baseline corresponding to absence of metallic objects, and analyzes the waveform with respect to opposite first and (Continued)

second thresholds. The controller activates the indicator in response to metallic objects passing through the coils when the waveform first exceeds the first threshold and then subsequently exceeds the second threshold.

20 Claims, 18 Drawing Sheets

Related U.S. Application Data continuation of application No. 16/062,138, filed as application No. PCT/US2016/068319 on Dec. 22, 2016, now Pat. No. 11,000,341.

(60) Provisional application No. 62/281,438, filed on Jan. 21, 2016, provisional application No. 62/387,198, filed on Dec. 23, 2015.

(51) Int. Cl.
| | |
|---|---|
| *A61B 50/30* | (2016.01) |
| *B09B 3/00* | (2022.01) |
| *B65F 1/14* | (2006.01) |
| *G01N 27/02* | (2006.01) |
| *G01V 3/10* | (2006.01) |

(52) U.S. Cl.
CPC ............ *A61B 50/3001* (2016.02); *B09B 3/00* (2013.01); *B09B 3/0075* (2013.01); *B65F 1/1415* (2013.01); *G01N 27/023* (2013.01); *G01V 3/104* (2013.01); *B65F 1/1473* (2013.01); *B65F 2210/1525* (2013.01); *B65F 2240/145* (2013.01)

(58) Field of Classification Search
USPC ...................................................... 340/686.4
See application file for complete search history.

(56) References Cited

U.S. PATENT DOCUMENTS

| | | | | |
|---|---|---|---|---|
| 4,486,713 | A | 12/1984 | Gifford | |
| 4,868,910 | A * | 9/1989 | Maulding | G01V 3/107 324/233 |
| 5,001,425 | A * | 3/1991 | Beling | B65F 1/14 340/568.1 |
| 5,034,689 | A | 7/1991 | Inoue et al. | |
| 5,576,621 | A | 11/1996 | Clements | |
| 5,610,516 | A * | 3/1997 | Maier | B65F 3/02 324/226 |
| 5,659,247 | A | 8/1997 | Clements | |
| 6,222,450 | B1 * | 4/2001 | Clements | B65F 1/1473 340/568.1 |
| 6,268,724 | B1 * | 7/2001 | Crowley | G01V 3/107 324/225 |
| 6,667,689 | B1 | 12/2003 | Steffen et al. | |
| 6,724,305 | B2 | 4/2004 | Edwards et al. | |
| 6,724,419 | B1 | 4/2004 | Green et al. | |
| 6,833,789 | B1 * | 12/2004 | Carmen | B65F 1/1607 340/552 |
| 7,296,683 | B1 * | 11/2007 | Vallelonga, Sr. | B65F 1/1607 209/636 |
| 7,893,690 | B2 | 2/2011 | Simon | |
| 9,637,309 | B2 * | 5/2017 | Starkey | B62B 3/04 |
| 9,840,369 | B2 | 12/2017 | Starkey et al. | |
| 10,077,153 | B2 | 9/2018 | Starkey et al. | |
| 11,000,341 | B2 | 5/2021 | Henniges et al. | |
| 2004/0000904 | A1 | 1/2004 | Cotter | |
| 2008/0297158 | A1 | 12/2008 | Heger et al. | |
| 2009/0284255 | A1 * | 11/2009 | Zur | G01R 33/04 324/239 |
| 2011/0156903 | A1 | 6/2011 | Henniges et al. | |
| 2013/0119978 | A1 * | 5/2013 | Freise | G01D 3/028 324/207.16 |
| 2013/0248395 | A1 * | 9/2013 | Guthrie | A61B 50/13 206/365 |
| 2017/0144836 | A1 | 5/2017 | Starkey et al. | |
| 2017/0144837 | A1 | 5/2017 | Starkey et al. | |
| 2018/0368933 | A1 | 12/2018 | Henniges et al. | |

FOREIGN PATENT DOCUMENTS

| | | | |
|---|---|---|---|
| JP | 860253892 | A | 12/1985 |
| JP | H01262494 | A | 10/1989 |
| JP | H05087941 | A | 4/1993 |
| JP | H05232247 | A | 9/1993 |
| JP | H07012953 | A | 1/1995 |
| JP | H08271640 | A | 10/1996 |
| JP | 2003167064 | A | 6/2003 |
| JP | 2006220500 | A | 8/2006 |
| JP | 2007203250 | A | 8/2007 |
| JP | 2010071821 | A | 4/2010 |
| JP | 2011149906 | A | 8/2011 |
| JP | 2014228522 | A | 12/2014 |
| WO | 2009052291 | A3 | 4/2009 |
| WO | WO-2009155107 | A2 * | 12/2009 ............. A61B 50/10 |

OTHER PUBLICATIONS

English language abstract for JPH 01-262494 A extracted from espacenet.com database on Mar. 10, 2023, 2 pages.
English language abstract and machine-assisted English translation for JPH 08-271640 A extracted from espacenet.com database on Mar. 10, 2023, 8 pages.
English language abstract and machine-assisted English translation for JP 2007-203250 A extracted from espacenet.com database on Mar. 10, 2023, 23 pages.
English language abstract and machine-assisted English translation for JP 2003-167064 A extracted from espacenet.com database on Dec. 3, 2020, 12 pages.
English language abstract and machine-assisted English translation for JP 2006-220500 extracted from espacenet.com database on Aug. 2, 2018, 18 pages.
English language abstract and machine-assisted English translation for JP 2010-071821 A extracted from espacenet.com database on Dec. 3, 2020, 24 pages.
English language abstract and machine-assisted English translation for JP 2011-149906 A extracted from espacenet.com database on Aug. 9, 2022, 15 pages.
English language abstract and machine-assisted English translation for JP 2014-228522 extracted from espacenet.com database on Aug. 2, 2018, 22 pages.
English language abstract and machine-assisted English translation for JPH 05-087941 A extracted from espacenet.com database on Dec. 3, 2020, 6 pages.
English language abstract and machine-assisted English translation for JPH 05-232247 A extracted from espacenet.com database on Aug. 9, 2022, 10 pages.
English language abstract and machine-assisted English translation for JPH 07-012953 A extracted from espacenet.com database on Dec. 3, 2020, 10 pages.
English language abstract and machine-assisted English translation for JPS 59-024282 A extracted from espacenet.com database on Dec. 3, 2020, 5 pages.
English language abstract and machine-assisted English translation for JPS 60-253892 A extracted from espacenet.com database on Aug. 9, 2022, 6 pages.
English language abstract for JPS 58-171690 A extracted from espacenet.com database on Aug. 9, 2022, 1 page.
International Search Report for Application No. PCT/US2015/068319 dated Apr. 13, 2017, 4 pages.

\* cited by examiner

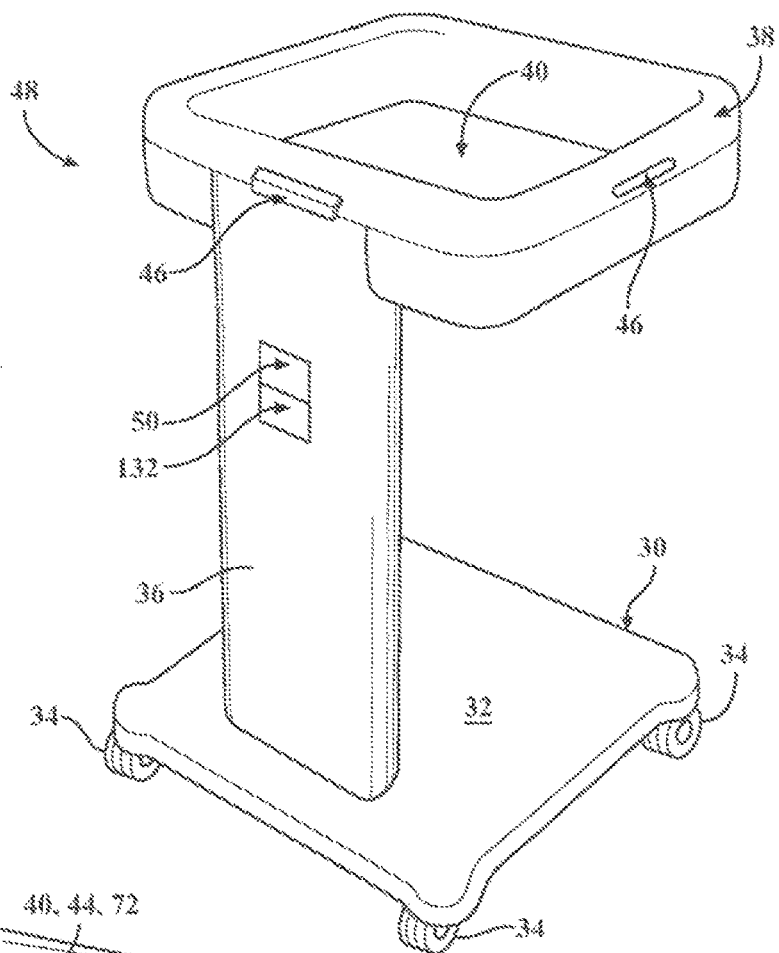

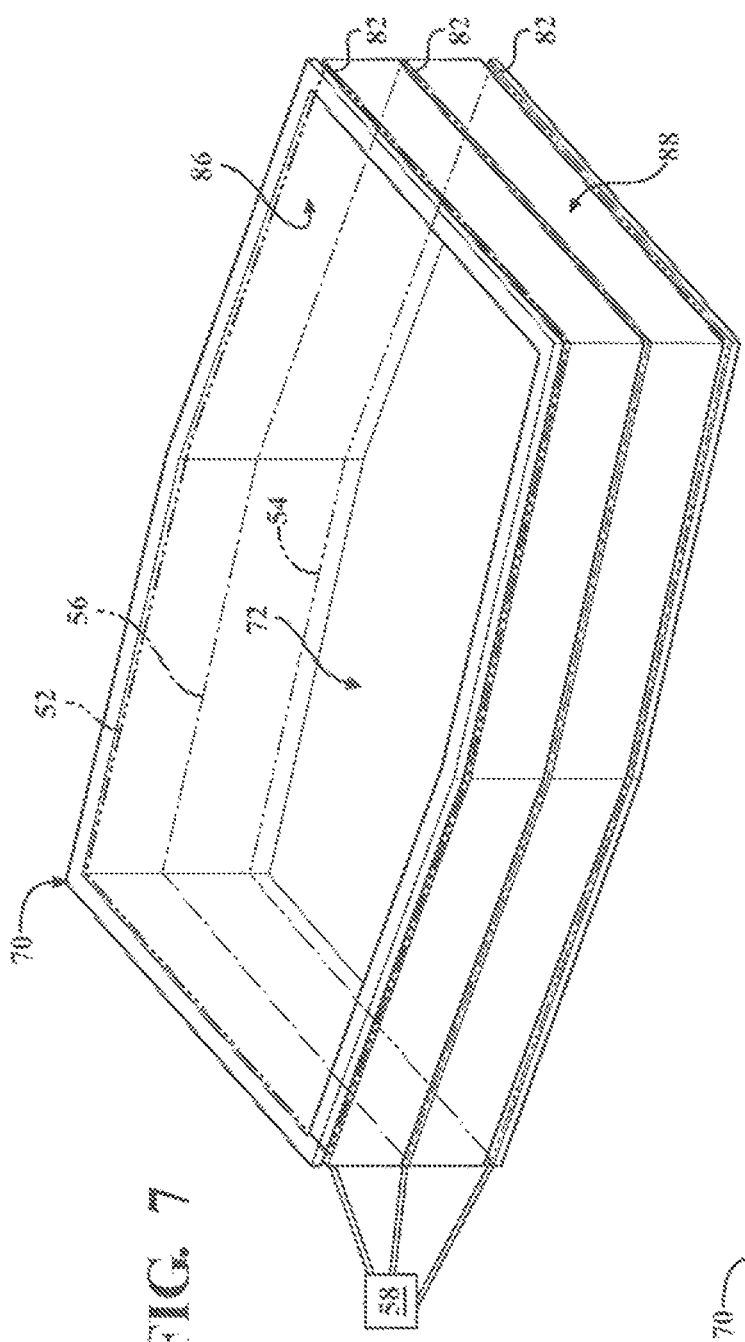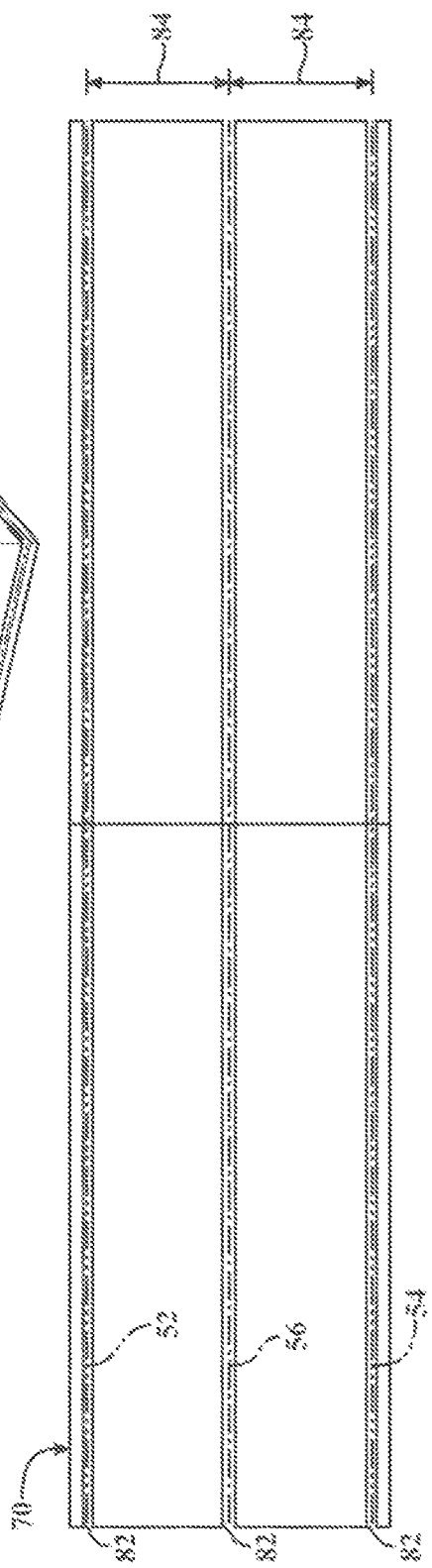
FIG. 7
FIG. 8

METAL DETECTION SYSTEM FOR USE WITH MEDICAL WASTE CONTAINER

CROSS-REFERENCE TO RELATED APPLICATIONS

The subject patent application is a continuation of U.S. patent application Ser. No. 17/314,463, filed May 7, 2021, which is a continuation of U.S. patent application Ser. No. 16/062,138, filed Jun. 14, 2018, which is a National Stage Entry of International Patent Application No. PCT/US2016/068319, filed Dec. 22, 2016, which claims priority to and all the benefits of U.S. Provisional Patent Application Ser. No. 62/387,198, filed Dec. 23, 2015, and U.S. Provisional Patent Application Ser. No. 62/281,438, filed Jan. 21, 2016, the disclosures of which are hereby incorporated herein by reference in their entirety.

TECHNICAL FIELD

The embodiments set forth herein relate, generally, to metal detection systems and, more specifically, to a metal detection system for use with a medical waste container.

BACKGROUND

Conventional medical practices and procedures typically involve the use of disposable articles and materials to maintain sterility and promote safety. Moreover, certain medical tools, instruments, and equipment may be sealed in disposable packaging to ensure sterility, or may otherwise employ disposable shields and/or covers. Thus, it will be appreciated that a relatively high amount of medical waste and trash can be generated during a complex medical procedure, such a surgical procedure where multiple medical devices, instruments, and tools are used and a high amount of disposable articles are consumed, such as gauze, tape, shields, table covers, drapes, tubing, padding, garments, and the like.

It will be appreciated that certain types of medical waste and trash generated during medical procedures can be extremely dangerous. By way of example, disposable articles contaminated with blood or human tissue may transmit infectious diseases to medical professionals, patients, or anyone involved in the handling and disposal of medical waste. Moreover, needles employed for drug administration, intravenous catheter insertion, and blood drawing are commonplace in the medical industry and are segregated from other types of medical waste and trash into so-called "sharps" containers.

While certain medical tools, instruments, and equipment are considered "disposable" and are discarded after one use, others can be re-used several times after being re-sterilized between medical procedures. By way of example, electrically-powered surgical tools may be decontaminated and re-sterilized in a high-pressure steam autoclave after use in a medical procedure. In order to facilitate multiple decontamination and sterilizations, re-usable tools are specially manufactured from robust materials and, thus, tend to be relatively expensive. Moreover, certain re-usable tools are designed to be lightweight to promote ease-of-use and improve handling, but may appear to be disposable to the untrained eye. Because of this, certain medical professionals, such as nurse's aides or cleaning staff members, may be unaware that certain medical tools are re-usable and should not be discarded with trash. Further, there is a tendency for inadvertent disposal of relatively small or lightweight objects that can become concealed in, around, or otherwise by larger objects, such as towel clips, scalpel handles or a needle concealed in a disposable surgical drapes.

In order to prevent inadvertent disposal of sharps and re-usable medical equipment along with other trash and medical waste, certain medical waste containers employ metal detectors adapted to alert a user of the presence of metallic objects, whereby an audible alarm typically sounds when metal is detected. However, medical waste metal detectors known in the art are often only designed to detect particular materials or certain types of objects, and may otherwise be unsuitable for use in certain environments. By way of example, certain medical waste metal detectors known in the art may be designed to detect small steel objects like needles and tend to be overly-sensitive which, in turn, frequently results in inadvertent activation of the alarm in response to transient movement of larger metal objects passing nearby, such as an IV pole. Further, known medical waste detectors may be designed to alert based on the presence of certain metals such as steel, but are unable to detect other types of metal frequently utilized in the medical industry, such as aluminum and titanium. Further still, known medical waste detectors may be unable to differentiate between a metallic object passing into the medical waste container, and a metallic object being subsequently removed from the medical waste container, and thus will unnecessarily alert when an inadvertently disposed metallic object is subsequently removed from the medical waste container.

For the foregoing reasons, there remains a need in the art for a metal detection system for medical waste containers that can identify inadvertently disposed metallic objects manufactured from different materials and which strikes a substantial balance between usability, functionality, and manufacturing cost while, at the same time, affording improved sensitivity and adaptability within different environments commonly encountered in the medical industry.

SUMMARY

In one embodiment, a detection system is provided for detecting disposal of metallic objects into an opening of a medical waste container. The detection system includes a detection indicator for indicating passage of metallic objects through the opening of the medical waste container. A pair of receive coils and a transmit coil spaced between the receive coils are provided. The coils are shaped for receiving waste therethrough adjacent to the opening of the medical waste container. A controller is provided in electrical communication with the coils. The controller is configured to generate a transmit signal and communicate the transmit signal to the transmit coil such that the transmit coil generates a magnetic field based on the transmit signal. The magnetic field induces voltage in each of the receive coils such that the receive coils each generate a receive signal received by the controller. The controller is further configured to generate a waveform based on both of the receive signals. The waveform has a baseline condition corresponding to absence of interaction of metallic objects with the magnetic field. The controller is still further configured to analyze the waveform with respect to a first detection threshold and a second detection threshold opposite to the first detection threshold with the baseline between the first detection threshold and the second detection threshold. The controller is further configured to activate the detection indicator in response to metallic objects passing through the coils based on the waveform exceeding the first detection threshold at a first time and exceeding the second detection threshold at a subsequent second time.

In another embodiment, a detection system is provided for detecting disposal of metallic objects into an opening of a medical waste container. The detection system includes a detection indicator for indicating passage of metallic objects through the opening of the medical waste container. A first receive coil, a second receive coil, and a transmit coil spaced between the receive coils are provided. The coils are shaped for receiving waste therethrough adjacent to the opening of the medical waste container. A controller is provided in electrical communication with the coils. The controller is configured to generate a transmit signal and communicate the transmit signal to the transmit coil such that the transmit coil generates a magnetic field based on the transmit signal. The magnetic field induces voltage in each of the receive coils such that the first receive coil generates a first receive signal and the second receive coil generates a second receive signal with both of the receive signals received by the controller. The controller is further configured to generate a waveform based on both of the receive signals. The waveform has a baseline condition corresponding to absence of interaction of metallic objects with the magnetic field. The controller is still further configured to analyze the waveform with respect to a first detection threshold and a second detection threshold opposite to the first detection threshold with the baseline between the first detection threshold and the second detection threshold. The controller is further configured to simultaneously analyze the receive signals and the waveform, and to activate the detection indicator in response to metallic objects passing through the coils based on predetermined changes occurring in the first receive signal and subsequent predetermined changes occurring in the second receive signal, and further based on the waveform exceeding the first detection threshold at a first time and exceeding the second detection threshold at a subsequent second time.

The detection system detects and alerts a user of disposal of metallic objects into an opening of a medical waste container, thereby significantly contributing to safety in handling trash and medical waste and affording increased opportunity for preventing inadvertent disposal of re-usable medical devices, instruments, and equipment while, at the same time, reducing the cost and complexity of manufacturing, assembling, and using medical waste container metal detection systems that provide users with improved functionality and usability.

BRIEF DESCRIPTION OF THE DRAWINGS

FIG. 1 is a front-side perspective view of a mobile cart having a detection system according to one embodiment.

FIG. 2 is a back-side perspective view of the mobile cart of FIG. 1 shown supporting a medical waste container having an opening.

FIG. 7 is a front-side perspective view of the coil support frame, transmit coil, and receive coils of FIG. 3.

FIG. 8 is a front-side plan view of the coil support frame, transmit coil, and receive coils of FIG. 3.

DETAILED DESCRIPTION

Figure 3:
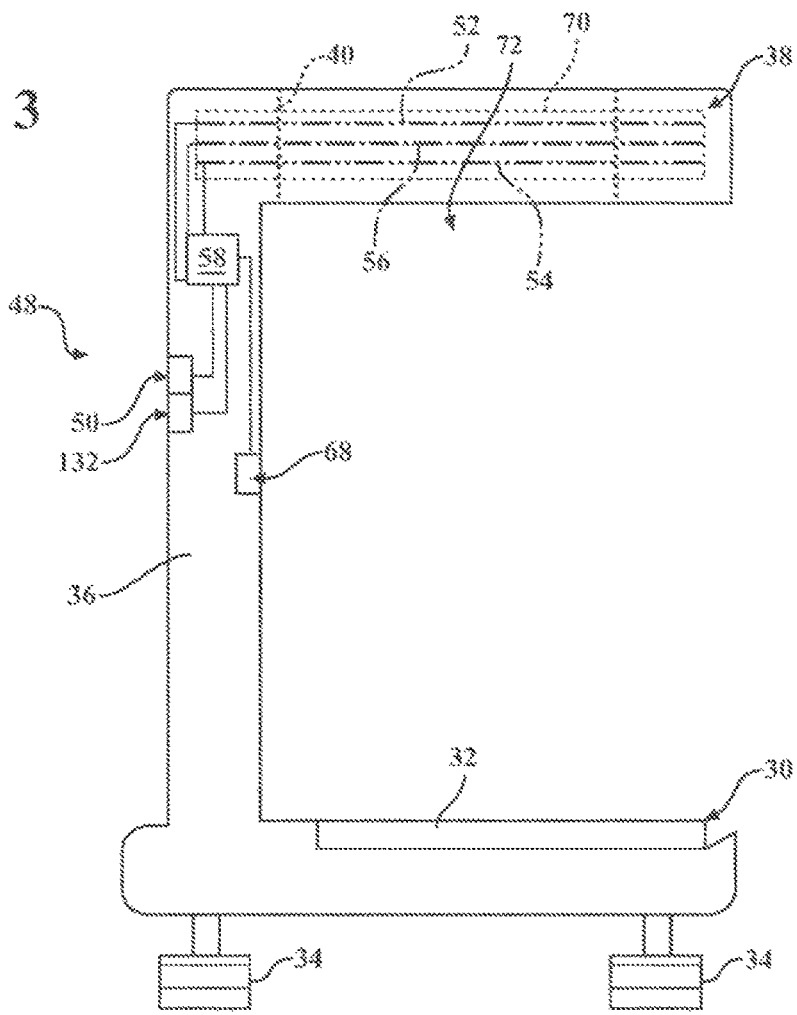
FIG. 3 is a right-side plan view of the cart and detection system of FIG. 1, having a coil support frame, a transmit coil, a first receive coil, a second receive coil, and a controller schematically shown in phantom.

With reference now to the drawings, wherein like numerals indicate like parts throughout the several views, a mobile cart is generally shown at 30 in FIGS. 1-6. The mobile cart 30 includes a base 32 supported by a plurality of wheels 34 employed to support the base 32 and facilitate mobility. A pedestal 36 is operatively attached to and extends above the base 32 (see FIG. 1). The pedestal 36 supports a mount, generally indicated at 38. In another embodiment, one or more additional pedestals 36 (not shown) can be added to improve the stiffness and reduce the deflection of the mount 38 when external loading is applied to the mount 38 during use. The mount 38 has a generally rounded-rectangular profile and defines a correspondingly-shaped aperture 40 shaped to accommodate a medical waste container 42 (see FIG. 2). However, it will be appreciated that the mount 38 and/or aperture 40 could have any suitable profile.

The medical waste container 42 may be removably attachable to the mount 38. The medical waste container 42 has an opening 44 secured adjacent to the aperture 40 of the mount 38. To that end, the mobile cart 30 may include one or more securing features, generally indicated at 46, employed to releasably secure the medical waste container 42 to the mount 38. In the representative embodiment illustrated herein, the medical waste container 42 is realized as a bag manufactured from plastic and configured to receive waste therein, such as garbage, trash, medical waste, and the like. However, as will be appreciated from the subsequent description below, the medical waste container 42 could be of any suitable type and could be configured in any suitable way sufficient to receive any type of waste. By way of non-limiting example, the medical waste container 42 could be realized with a conventional "garbage can" with a rigid body and with or without a disposable bag. The medical waste container 42 may be transparent to facilitate retrieval of inadvertently disposed metallic objects, and/or may be tinted certain colors corresponding to the type of medical waste intended to be contained therein.

The mobile cart 30 and/or the medical waste container 42 employs a detection system, generally indicated at 48, according to one embodiment, for detecting disposal of metallic objects into the opening 44 of the medical waste container 42. In some embodiments, the mobile cart 30 is optional. As shown schematically in FIG. 3, the detection system 48 includes a detection indicator 50, a first receive coil 52, a second receive coil 54, a transmit coil 56, and a controller 58. The detection indicator 50 is employed to indicate passage of metallic objects through the opening 44 of the medical waste container 42. In one embodiment, the detection indicator 50 includes at least one audible and/or visual indicator, such as one or more speakers, displays, lights, and the like.

In the illustrated embodiment, the transmit coil 56 is spaced between the receive coils 52, 54. The coils 52, 54, 56 are shaped for receiving waste there through adjacent to the opening 44 of the medical waste container 42, as described in greater detail below (waste container 42 not shown in FIG. 3). The controller 58 is disposed in electrical communication with the coils 52, 54, 56. The controller 58 is configured to generate a transmit signal 60 (see, e.g., FIG. 11A) and communicate the transmit signal 60 to the transmit coil 56 such that the transmit coil 56 generates a magnetic field based on the transmit signal 60. The magnetic field, in turn, induces voltage in each of the receive coils 52, 54 such that the first receive coil 52 generates a first receive signal 62 (see, e.g., FIG. 11B) received by the controller 58 and the second receive coil 54 generates a second receive signal 64 (see, e.g., FIG. 11C) received by the controller 58. As is explained in greater detail below, the controller 58 is configured to generate a waveform 66 based on both of the receive signals 62, 64, and is further configured to analyze the waveform 66 to detect the passage of metallic objects through the opening 44 of the medical waste container 42 based at least partially on predetermined changes occurring in the receive signals 62, 64. As will be appreciated from the subsequent description below, "predetermined changes" of the receive signals 62, 64 could include changes in amplitude, magnitude, frequency, and/or shift in phase.

With continued reference to FIG. 3, the detection system 48 employed by the mobile cart 30 is configured to alert a user when a metallic object passes through the coils 52, 54, 56 into the opening 44 of the medical waste container 42. In one embodiment, the detection system 48 includes a power source 68 (shown schematically in FIG. 3) disposed in electrical communication with the controller 58 to facilitate operation of the detection system 48. In one embodiment, the power source 68 is realized as a rechargeable battery. However, those having ordinary skill in the art will appreciate that the power source 68 could be of any suitable type or configuration sufficient to operate the detection system 48.

As is depicted schematically in FIG. 3, in one embodiment, the detection system 48 is operatively attached to and is supported by the mobile cart 30. To this end, in one embodiment, the detection system 48 includes a coil support frame 70 arranged to support the coils 52, 54, 56, as described in greater detail below. The coil support frame 70 is operatively attached to the mount 38 of the mobile cart 30 or other support structure, and may be manufactured from one or more components which cooperate to support, retain, or otherwise align the coils 52, 54, 56. The coil support frame 70 may be fixed to the mount 38 with adhesive, non-metallic fasteners, and the like. The mount 38 may be formed of plastic to limit interference (for example, electromagnetic interference) with the operation of the coils 52, 54, 56 and the detection system 48. It will be appreciated that the detection system 48 described herein could be used in a number of different applications, such as with mobile carts 30 without wheels 34, with mounts 38 configured to walls or other immobile structures, and the like. By way of non-limiting example, the detection system 48 could employ a mount 38 adapted to be coupled to a wall so as to support the coils 52, 54, 54 vertically above a medical waste container 42 realized as conventional rigid garbage can with a disposable bag.

Referring now to FIGS. 3-6, the coil support frame 70 defines a passage 72 through which the medical waste container 42 is positionable to receive waste, as noted above. Here, the aperture 40 of the mount 38 is aligned with respect to the passage 72 of the coil support frame 70 such that objects passing through the opening 44 of the medical waste container 42 also pass through the aperture 40 of the mount 38 and the passage 72 of the coil support frame 70. Thus, objects passing through the opening 44 of the medical waste container 42 pass sequentially through the first receive coil 52, the transmit coil 56, and the second receive coil 54 while being received in the medical waste container 42. In one embodiment, the mount 38 has internal walls 74 spaced from the aperture 30 to define a hollow space, generally indicated at 76, within which the coil support frame 70 is supported (see FIGS. 5 and 6). Here, the coils 52, 54, 56 are arranged between the internal walls 74 and the aperture 40 of the mount 38.

Figure 5:
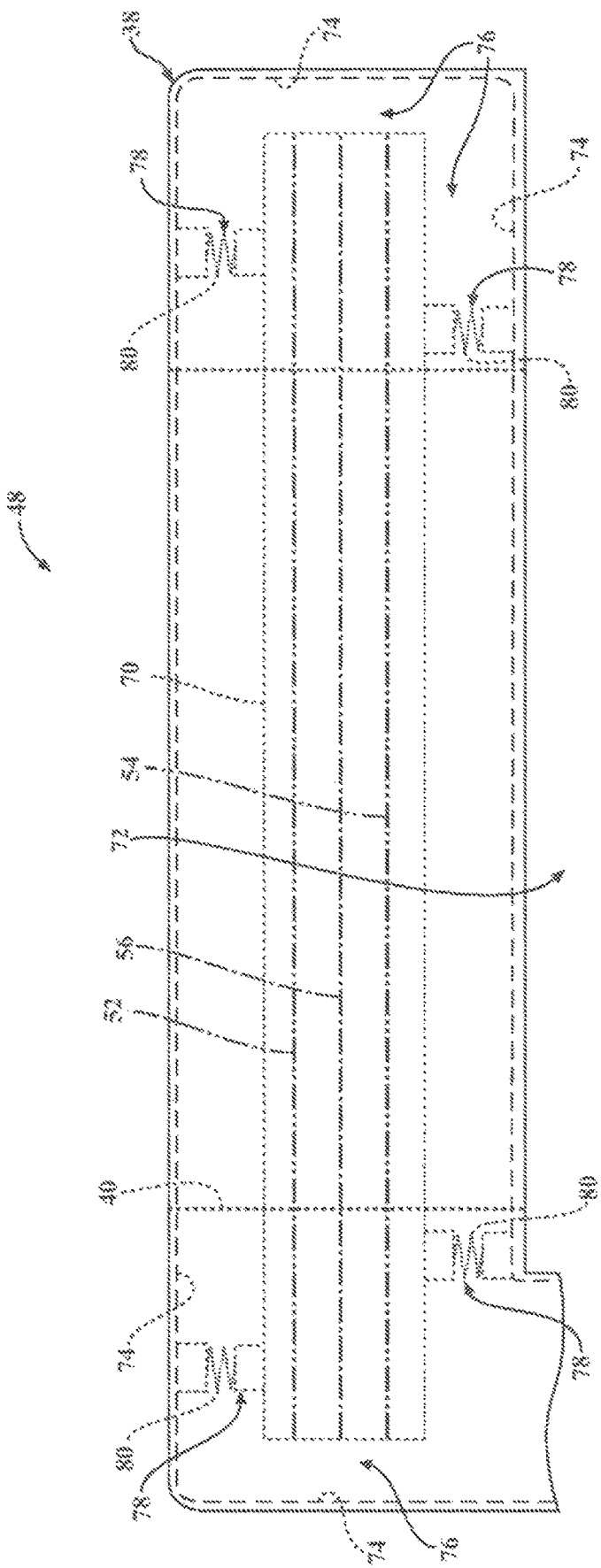
FIG. 5 is an enlarged partial right-side plan view of the cart and detection system of FIG. 3, depicting an isolation mechanism shown in phantom interposed between the coil support frame and the cart.
Figure 6:
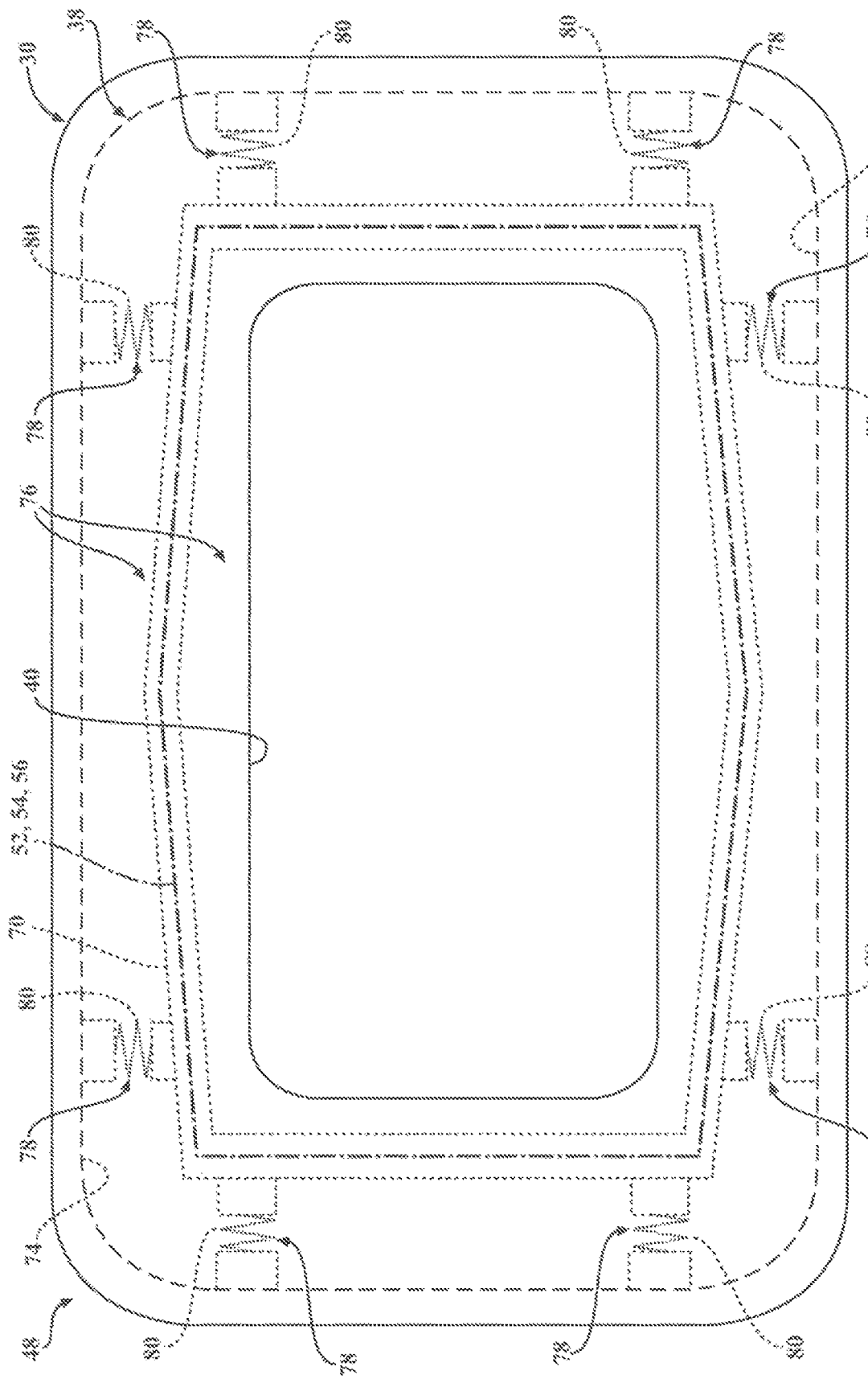
FIG. 6 is a top-side plan view of the cart and detection system of FIG. 3, depicting an isolation mechanism shown in phantom interposed between the coil support frame and the cart.

In one embodiment, an isolation mechanism 78 is interposed between the mount 38 and the coil support frame 70 to isolate the coil support frame 38 from external force acting on the mount 38 (see FIGS. 5 and 6). More specifically, the isolation mechanism 78 prevents external forces acting on the mobile cart 30 or other supporting structure from deflecting or changing the position of the coils 52, 54, 56 relative to each other. It will be appreciated that external forces may occur during use in a number of different ways, such as by objects placed on top of the mobile cart 30, people or objects "bumping" or otherwise engaging the mobile cart 30, and the like. Here, the isolation mechanism 78 is advantageously positioned, arranged, and configured so as to isolate the coil support frame 70 from external forces acting on the mobile cart 30 in multiple directions, such as vertical (see FIG. 5) and horizontal (see FIG. 6). To this end, the isolation mechanism 78 may be realized as one or more discrete components coupled to the internal walls 74 and to the coil support frame 70 at one or more predetermined locations so as to dampen, attenuate, reduce, or otherwise inhibit the transmission of external force to the coil support frame 70.

In the representative embodiment illustrated herein, the isolation mechanism 78 comprises a resilient member 80 operatively attached to the mount 38 and to the coil support frame 70. However, those having ordinary skill in the art will appreciate that the isolation mechanism 78 could comprise any suitable type and/or arrangement of components sufficient to isolate the coil support frame 70 from external forces acting on the mount 38. By way of non-limiting example, the isolation mechanism 78 could comprise various arrangements of resilient materials, elastomeric materials, cushioning materials, biasing members, and the like, such as foam or rubber.

Figure 4:
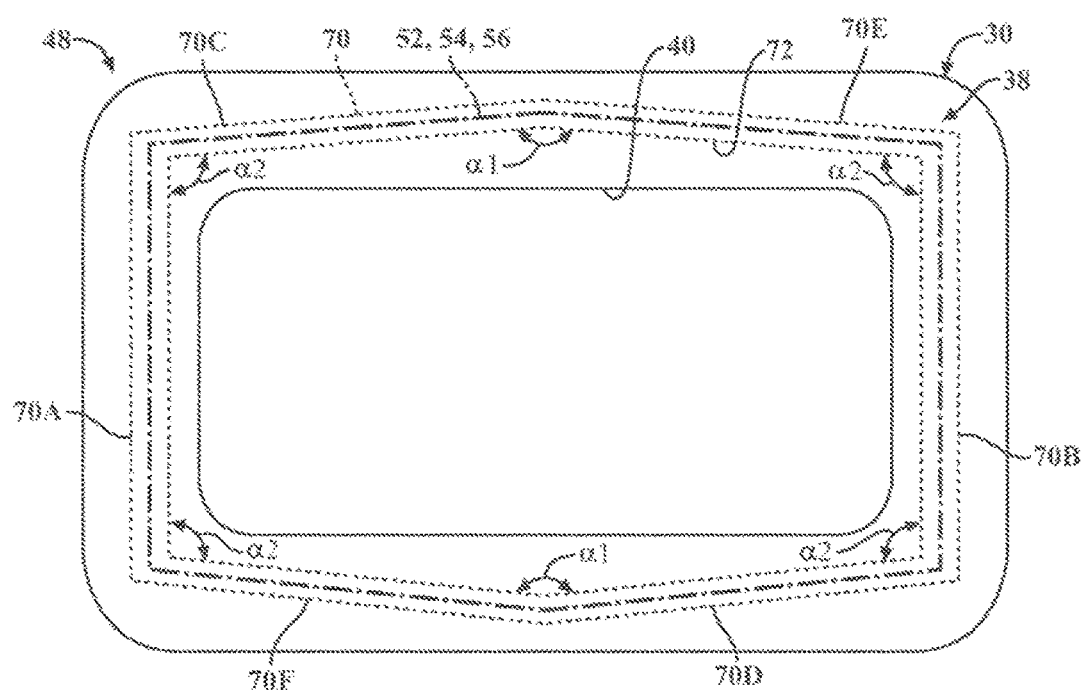
FIG. 4 is a top-side plan view of the cart and detection system of FIG. 3.

Referring now to FIGS. 3-10, in the representative embodiment illustrated herein, the coil support frame 70 has a profile defined by a generally polygonal shape surrounding the aperture 40 of the mount 38 (see FIG. 4). Here, the coils 52, 54, 56 each have a profile that is complimentary to the profile of the coil support frame 70. Specifically, the coil support frame 70 and the coils 52, 54, 56 each have a profile defined as an irregular hexagon with at least one pair of parallel and diametrically opposed straight sides. However, it will be appreciated that the coil support frame 70 and/or the coils 52, 54, 56 could alternatively have a round or oval profile, or any other suitable profile. In the embodiment shown in FIG. 4, the coil support frame 70 has two parallel and diametrically opposed straight sides 70A, 70B, two parallel and diametrically offset straight sides 70C, 70D, and two additional parallel and diametrically offset straight sides 70E, 70F. Here, sides 70C and 70E as well as sides 70D and 70F join at a vertex having an angle $\alpha 1$ which is greater than an angle $\alpha 2$ of a vertex between sides 70A and 70C, sides 70A and 70F, sides 70B and 70E, and sides 70B and 70D. Here, angle $\alpha 2$ is greater than 90° and angle $\alpha 1$ is less than 180°. Specifically, as shown in FIG. 4, $\alpha 2$ is approximately 95° and angle $\alpha 1$ approximately 170°.

As explained in greater detail below, in one embodiment, the coils 52, 54, 56 of the detection system 48 are advantageously physically balanced with respect to each other so as to enhance sensitivity and detection accuracy in operation. To that end, in the representative embodiment illustrated herein, the coils 52, 54, 56 are supported in respective grooves 82 defined in the coil support frame 70. The grooves 82 are arranged to support the coils 52, 54, 56 and, thus, effect physical balance through symmetry therebetween. Here, as best shown in FIGS. 3, 4, and 8, the coils 52, 54, 56 are aligned so as to be parallel with each other and are arranged so as to be co-axial with each other. Moreover, the coils 52, 54, 56 have a common profile with a common shape and common perimeter (see FIG. 8), and the transmit coil 56 is spaced equidistantly between the receive coils 52, 54. In one aspect, each of the coils 52, 54, 56 includes the same number of turns of a conductive wire, such as copper (not shown in detail). In another aspect, each of the receive coils 52, 54 includes at least fifty turns of conductive wire (not shown in detail). In another aspect, each of the receive coils includes at least twenty-five turns of conductive wire. It will be appreciated that coils 52, 54, 56 made from the same length of the same type and size of wire and positioned within the same electromagnetic environment will have the same electrical inductance, impedance, and capacitance. In one embodiment, transmit coil 56 could have a different number of turns and thus different electrical characteristics than receive coils 52, 54. Moreover, while the representative embodiment of the detection system 48 described herein and illustrated throughout the drawings employs a single transmit coil 56 arranged between the receive coils 52, 54, as will be appreciated from the subsequent description below, the detection system 48 could employ multiple transmit coils 56, operating at the same frequency or at different frequencies, arranged between the receive coils 52, 54 in various manners.

As shown in FIG. 8, in one embodiment, the coils 52, 54, 56 are spaced from each other at a predetermined distance 84 between 20 mm and 50 mm. In another embodiment, the predetermined distance 84 is between 40 mm and 60 min. In yet another embodiment, the predetermined distance 84 is advantageously 50 mm. However, those having ordinary skill in the art will appreciate that the predetermined distance 84 could be any suitable distance, and could be adjusted for specific application requirements, such as to accommodate medical waste containers 42 of different types, sizes, shapes, and/or configurations. Moreover, it will be appreciated that the coils 52, 54, 56 and the predetermined distance 84 are depicted schematically and/or illustratively throughout the drawings, are not drawn to scale, and are not intended to be used as a dimensional or spatial reference with respect to any other part of the detection system 48, unless otherwise specified herein.

As noted above, the grooves 82 formed in the coil support frame 70 align and support the coils 52, 54, 56. In the representative embodiment illustrated in FIGS. 3-10, the coil support frame 70 is formed as a unitary, one-piece component having an inner surface 86 and an outer surface 88 (see FIG. 7), with the inner surface 86 defining the passage 72 and with the grooves 82 formed in the outer surface 88. It will be appreciated that this configuration contributes to ease of manufacturing of the detection system 48 in that all of the coils 52, 54, 56 are supported by a common coil support frame 70 in respective grooves 82 arranged at the predetermined distance 84. Put differently, this configuration effects the physical alignment of the coils 52, 54, 56 noted above in a simple, cost-effective manner. However, those having ordinary skill in the art will appreciate that the coil support frame 70 could be manufactured from or otherwise realized as any suitable number of components which cooperate to support the coils 52, 54, 56. By way of non-limiting example, the coil support frame 70 could be realized as three discrete members each supporting a respective coil 52, 54, 56 and coupled together for concurrent movement. In some embodiments, the coil support frame 70 is relatively rigid so as to resist deflection, which helps to maintain the arrangement, orientation, and spacing of the coils 52, 54, 56 with respect to each other. Here, it will be appreciated that the rigidity of the coil support frame 70 and the isolation mechanism 78 each contribute to preventing deflection and/or relative movement of the coils 52, 54, 56 during use.

Figure 9A:
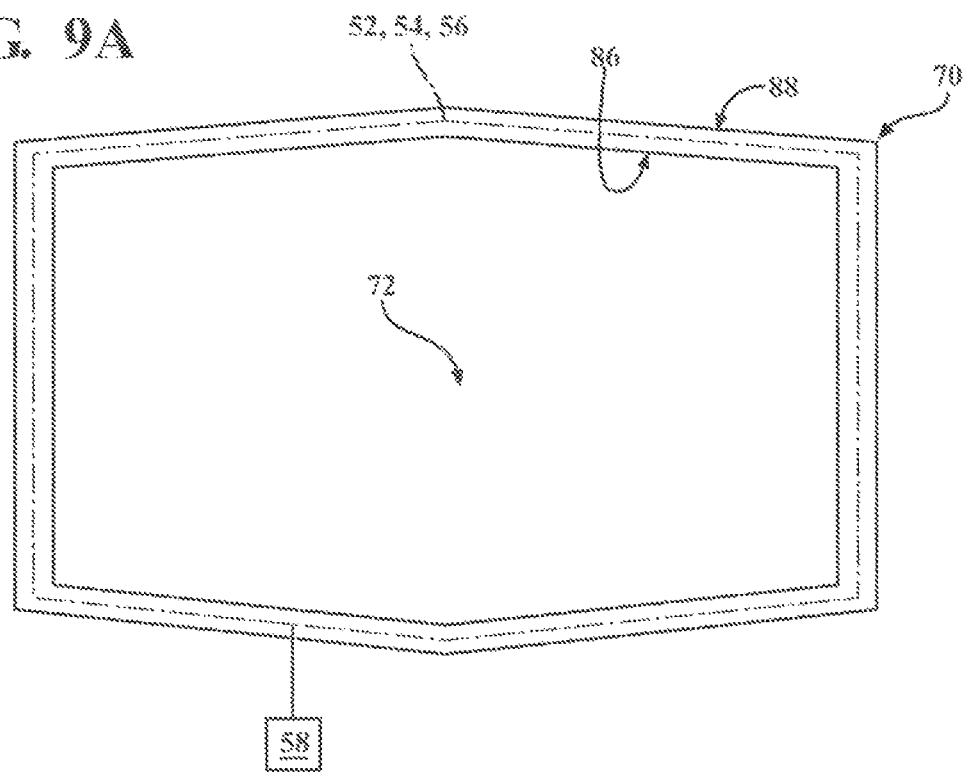
FIG. 9A is a top-side plan view of the coil support frame of FIG. 3.
Figure 9B:
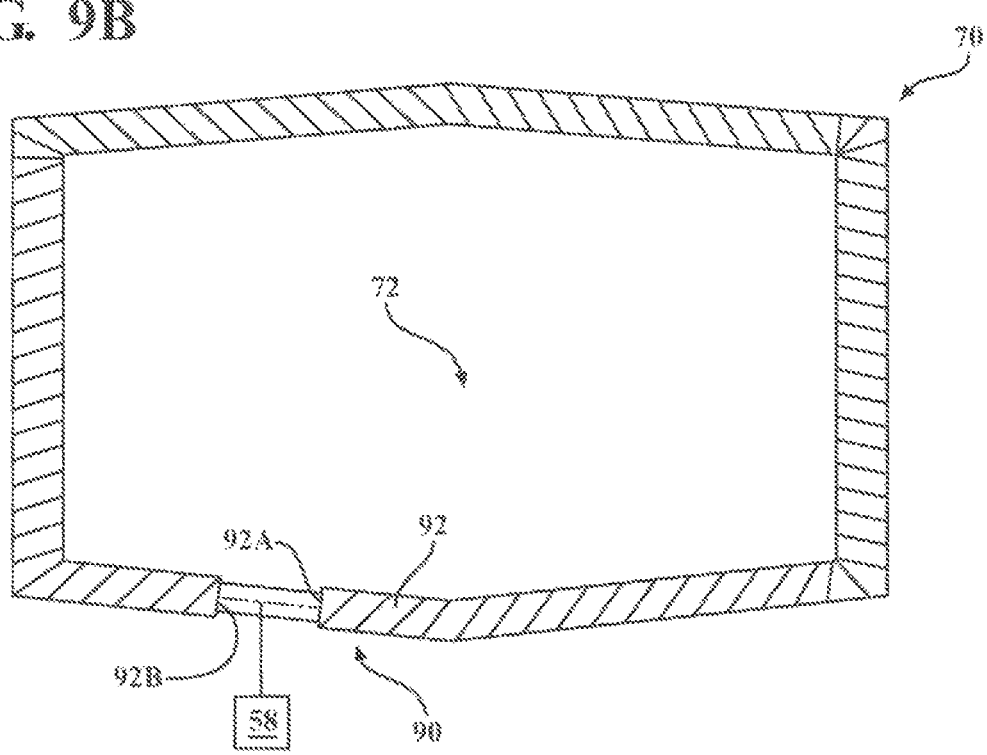
FIG. 9B is a top-side plan view of the coil support frame of FIG. 9A shown with a first faraday arrangement disposed about the coil support frame between spaced-apart first ends.

Referring now to FIGS. 9A-9E, the coil support frame 70 of FIGS. 3-8 is shown supporting the coils 52, 54, 56 (depicted schematically in FIG. 9A). In one embodiment, the detection system 48 comprises a faraday shield, generally indicated at 90, configured to shield the receive coils 52, 54 from external electrical fields. To this end, the faraday shield 90 comprises a first faraday arrangement 92 (see FIG. 9B-9E), insulators 94 (see FIGS. 9C-9E), and a second faraday arrangement 96 (see FIGS. 9D-9E). As best shown in FIG. 9B, the first faraday arrangement 92 comprises a strip of material, such as copper or aluminum, which is "wrapped" around the outer surface 88 and the inner surface 86 of the coil support frame 70 in an overlapping arrangement between spaced-apart first ends 92A, 92B.

Figure 9C:
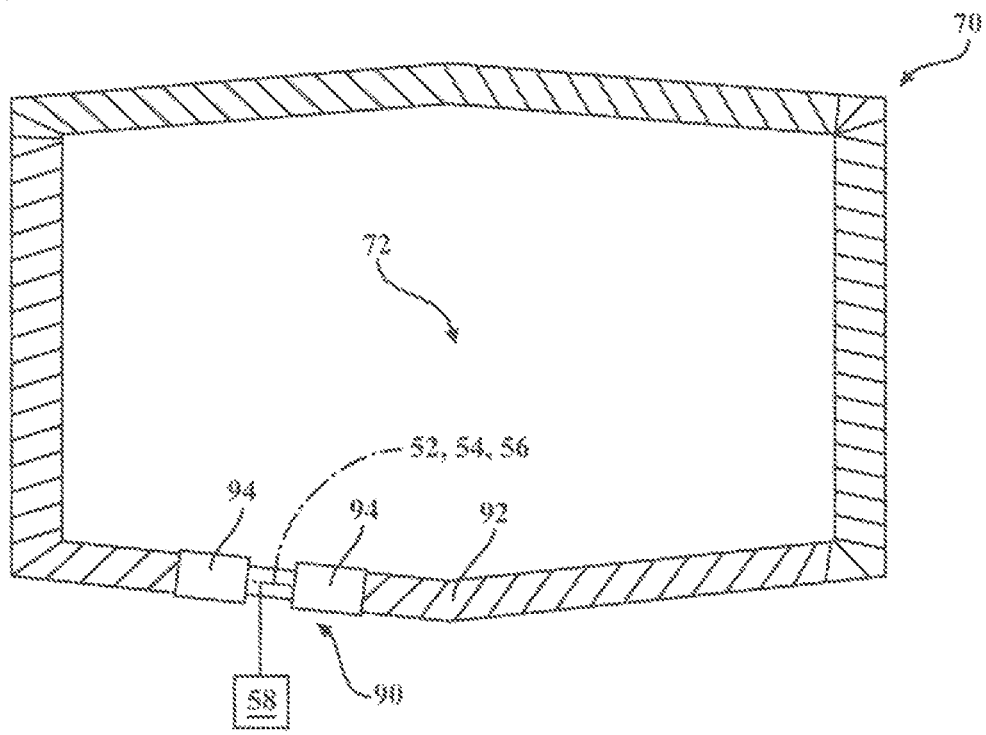
FIG. 9C is a top-side plan view of the coil support frame and first faraday arrangement of FIG. 9B shown with insulators disposed at each of the first ends.

As best shown in FIG. 9C, insulators 94 are provided at each of the first ends 92A, 92B. The insulators 94, which may be realized as one or more "wraps" of insulating tape, are provided to prevent electrical contact across the first ends 92A, 92B of the first faraday arrangement 92, as well as to prevent contact between the first faraday arrangement 92 and the second faraday arrangement 96.

Figure 9D:
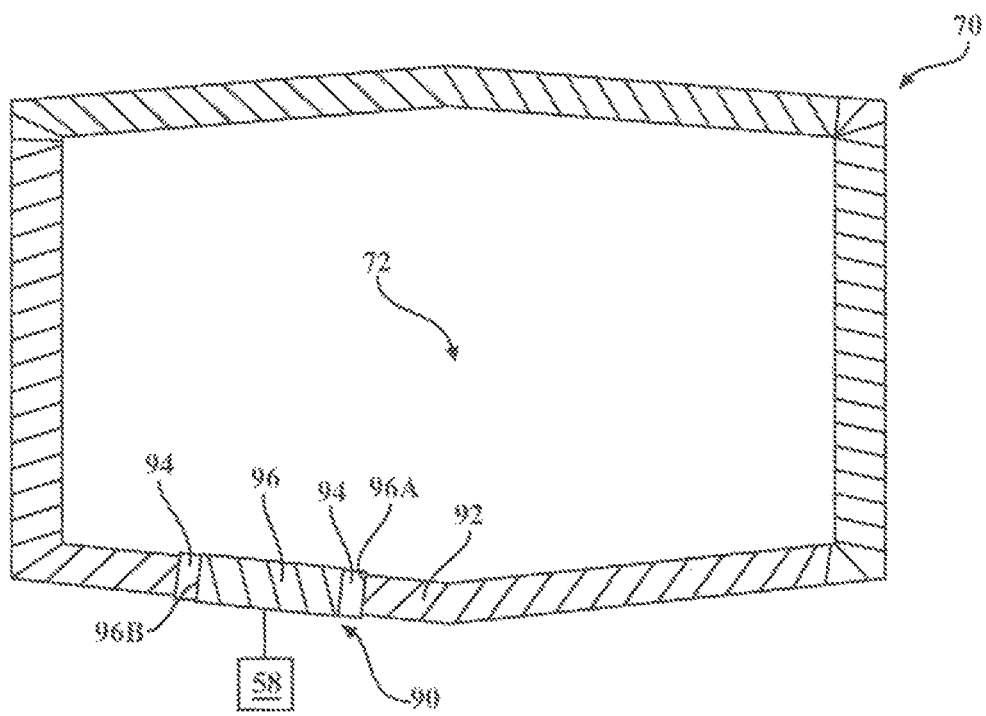
FIG. 9D is a top-side plan view of the coil support frame, first faraday arrangement, and insulators of FIG. 9C shown with a second faraday arrangement disposed about the coil support adjacent to the insulators at each of the first ends.

As illustrated in FIG. 9D, the second faraday arrangement 96 similarly comprises a strip of material, such as copper or aluminum, which is "wrapped" around or otherwise encompasses the outer surface 88 and the inner surface 86 of the coil support frame 70 in an overlapping arrangement between spaced-apart second ends 96A, 96B. Here, the second faraday arrangement 96 is wrapped over the insulators 96 so as to encompass the first ends 92A, 92B of the first faraday arrangement 92 such that the entire coil support frame 70 (and, thus, all portions of each of the receive coils 52, 54) is "wrapped" or otherwise encompassed by either the first faraday arrangement 92 and/or the second faraday arrangement 96.

While the faraday shield 90 described above and illustrated in FIGS. 9B-9E is configured to encompass both of the receive coils 52, 54, it will be appreciated that each of the receive coils 52, 54 could be provided with a respective faraday shield 90, such as may be implemented where the coil support frame 70 is comprised of discrete components supporting the respective coils 52, 54, 56, as noted above. Moreover, while the faraday arrangements 92, 96 described herein each comprise "wrapped" strips of material such as copper or aluminum alloys, it will be appreciated that other materials, such as any suitable non-magnetic and electrically-conductive material, as well as different types or configurations of faraday arrangements 92, 96 and/or insulators 94, could be utilized for certain applications.

Figure 9E:
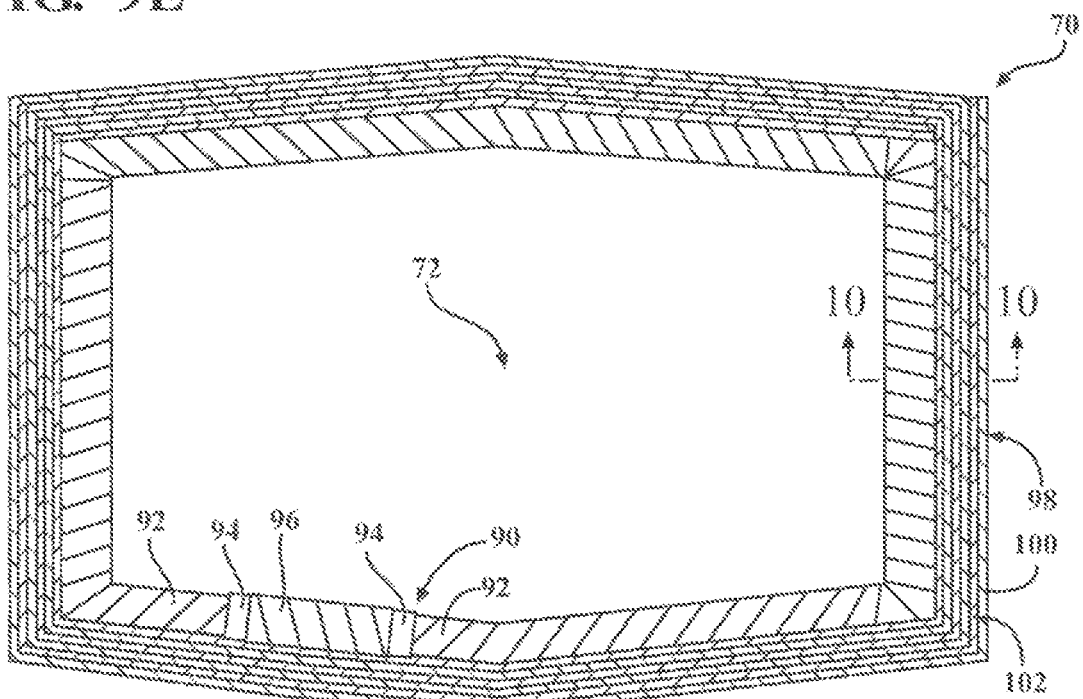
FIG. 9E is a top-side plan view of the coil support frame, faraday arrangements, and insulators of FIG. 9D shown with a field shaping arrangement disposed about the coil support frame.
Figure 10:
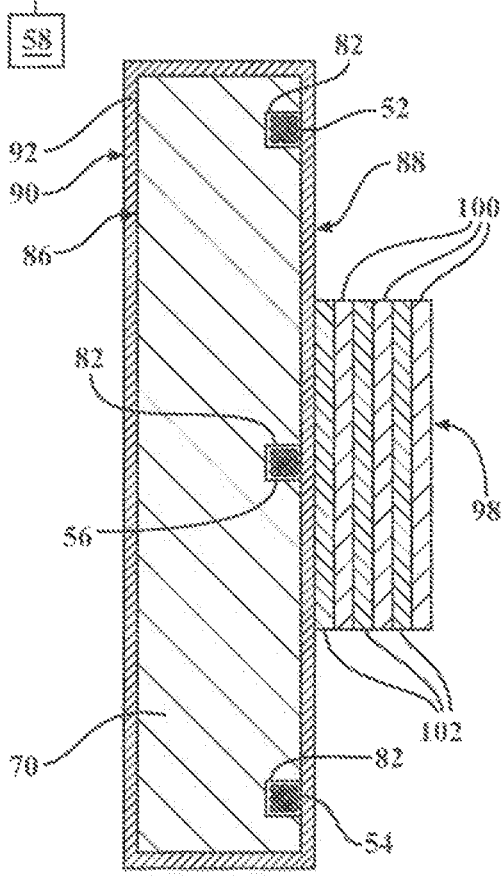
FIG. 10 is a sectional view taken along line 10-10 of FIG. 9E.

Referring now to FIGS. 9E and 10, in one embodiment, the detection system 48 comprises a field shaping arrangement, generally indicated at 98, configured to shape magnetic fields generated by the transmit coil 56 during use, as is described in greater detail below, so as to direct, focus, or otherwise concentrate the magnetic field towards the passage 72 of the coil support frame 70 and away from the outside environment. To this end, the field shaping arrangement 98 comprises a strip of magnetic field shaping material 100 and a strip of insulating material 102, which are "wrapped" around or otherwise encompasses the outer surface 88 of the coil support frame 70. Here, the field shaping arrangement 98 is operatively attached to the coil support frame 70 so as to remain in a fixed position and orientation relative to the coils 52, 54, 56 during use. Here, too, the rigidity of the coil support frame 70 and the isolation from external forces afforded by the isolation mechanism 78 contribute to preventing deflection or relative movement of the field shaping arrangement 98 relative to the coils 52, 54, 56 during use. In the representative embodiment illustrated herein, three "loops" of each of the materials 100, 102 are provided adjacent to the transmit coil 56 and relative to the receive coils 52, 54. As shown in FIG. 10, the field shaping arrangement 98 is disposed vertically between the receive coils 52, 54. However, other configurations and arrangements could be used. The insulating material 102 is provided to prevent physical contact between the "loops" of the magnetic field shaping material 100. While three "loops" of each of the materials 100, 102 are shown in the representative embodiment depicted in FIGS. 9E and 10, those having ordinary skill in the art will appreciate that more or fewer "loops" could be employed, depending on application requirements and the specific configuration of the field shaping arrangement 98, such at the size, shape, and/or magnetic permeability of the magnetic field shaping material 100.

The magnetic field shaping material 100 is configured, shaped, and arranged so as to direct, focus, or otherwise concentrate the magnetic field towards the passage 72 of the coil support frame 70, as noted above. To this end, the magnetic field shaping material 100 may be comprised of a suitable material such as CarTech® High Permeability "49"® Alloy which, when treated, forms an oxide layer which may serve as the insulating material 102 noted above. However, those having ordinary skill in the art will appreciate that the field shaping arrangement 98 could be configured in a number of different ways and could comprise any suitable type of magnetic field shaping material 100 and/or insulating material 102.

As is described in greater detail below, the waveform 66 has a baseline 104 condition corresponding to absence of interaction of metallic objects within the magnetic field generated by the transmit coil 56. Here, because the waveform 66 can be generated by the controller 58 in a number of different ways, those having ordinary skill in the art will appreciate that the baseline 104 can similarly be defined in different ways. By way of non-limiting example, the baseline 104 could represent zero voltage and the waveform 66 could change in amplitude from the baseline 104 between various positive and negative voltages over time. Thus, it will be appreciated that the baseline 104 can be defined in any suitable way, and the waveform 66 can be generated based on any suitable parameter which changes with respect to the baseline 104 where the baseline 104 is established when there is no metal interacting with the magnetic field generated by the transmit coil 56, in any suitable domain sufficient to detect the passage of metallic objects into the opening 44 of the medical waste container 42, as noted above. In one embodiment, the waveform 66 baseline 104 could include a DC offset voltage greater than zero.

Figure 11A:
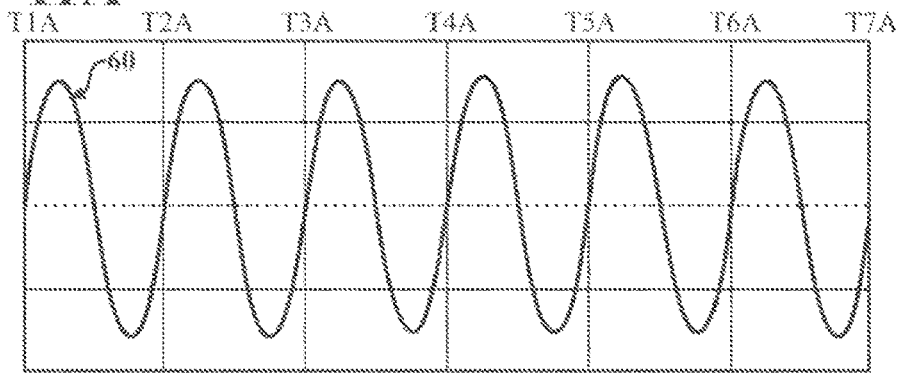
FIG. 11A is a graph depicting a transmit signal generated by the controller and communicated to the transmit coil of the detection system of FIG. 3.
Figure 11B:
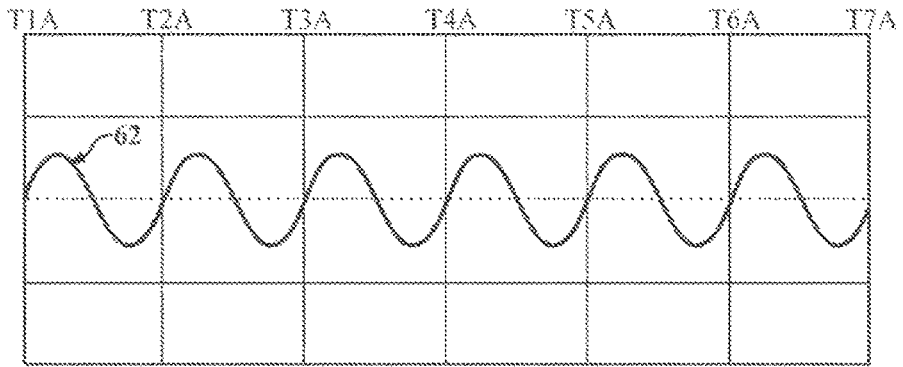
FIG. 11B is a graph depicting a first receive signal generated in the first receive coil and received by the controller of FIG. 3, representing an absence of metallic objects adjacent to the detection system.

Referring now to FIGS. 11A-11B, various graphs are depicted. Here, for the purposes of clarity and consistency, unless otherwise indicated, each of these graphs are plotted horizontally with respect to time and vertically with respect to a voltage which is offset from zero. As such, in the description which follows, phrases such as "increasing amplitude" indicate a voltage moving away from zero over time in a positive direction (for example, from 1 v to 2.5 v), while phrases such as "decreasing amplitude" indicate a voltage moving towards zero over time in a negative direction (for example, 2.5 v to 1 v). It will be appreciated that this nomenclature is used herein for the non-limiting purposes of clarity and consistency.

Referring now to FIGS. 11A-11D, a set of graphs are shown along a common time scale delineated between seven equally-spaced time references T1A, T2A, T3A, T4A, T5A, T6A, and T7A. Here, the graphs respectively represent the transmit signal 60 in the transmit coil 56 (see FIG. 11A), the first receive signal 62 in the first receive coil 52 (see FIG. 11B), the second receive signal 64 in the second receive coil 54 (see FIG. 11C), and the waveform 66 generated by the controller 58 based on the receive signals 62, 64 (see FIG. 11D) during an operating condition of the detection system 48. The baseline 104 condition of the waveform 66 corresponds to absence of interaction of metallic objects with the magnetic field, as noted above. Here, the transmit signal 60 is a sinusoidal oscillating voltage and the magnetic field is an alternating magnetic field. As will be appreciated from the subsequent description below, this sinusoidal transmit signal 60 can be operated at different power levels, voltages, and frequencies depending on characteristics such as the size of the opening 70, the size and type of metallic items targeted for detection and size, the type of the power source 68 used to operate the system, and the like. In one embodiment, the transmit signal operating frequency is between 5 KHz and 71 KHz. In one embodiment, the transmit signal operating frequency is between 7 KHz and 25 KHz. In another embodiment, the transmit signal operating frequency is less than or equal to 24 KHz. In one embodiment, the transmit signal operating frequency is 7 KHz for a battery operated system.

Figure 11C:
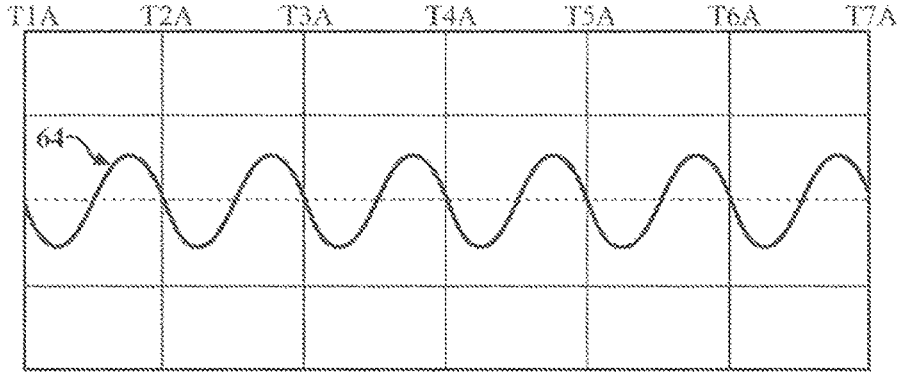
FIG. 11C is a graph depicting a second receive signal generated in the second receive coil and received by the controller of FIG. 3, representing an absence of metallic objects adjacent to the detection system.

The first receive signal 62 shown in FIG. 11B and the second receive signal 64 shown in FIG. 11C are equal and opposite to each other from the first time reference T1A to the seventh time reference T7A (compare amplitude, frequency, and phase shown in FIGS. 11B and 11C). Thus, because no imbalance occurs between the receive signals 62, 64, the resulting waveform 66 generated by the controller 58 is shown as a substantially flat line from the first time reference T1A to the seventh time reference T7A so as to indicate that the baseline 104 remains substantially constant over time (see FIG. 11D). Put differently, the baseline 104 has zero amplitude (no AC component) during this operating condition. Here, the receive signals 62, 64 are summed to create the resulting waveform 66. More specifically, because of the electrical balancing and physical symmetry of the coils 52, 54, 56 and the absence of interaction of metallic objects with the magnetic field, no imbalance occurs between the first receive signal 62 and the second receive signal 64 here and, thus, the waveform 66 remains at the baseline 104 from first time reference T1A to the seventh time reference T7A.

Figure 12A:
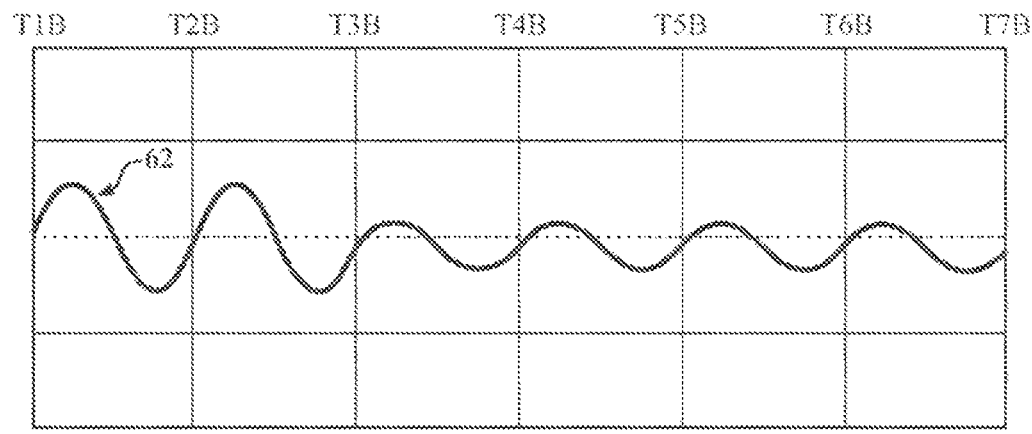
FIG. 12A is a graph depicting an alternate instance of the first receive signal of FIG. 11B, representing a metallic object brought nearby the detection system.
Figure 12B:
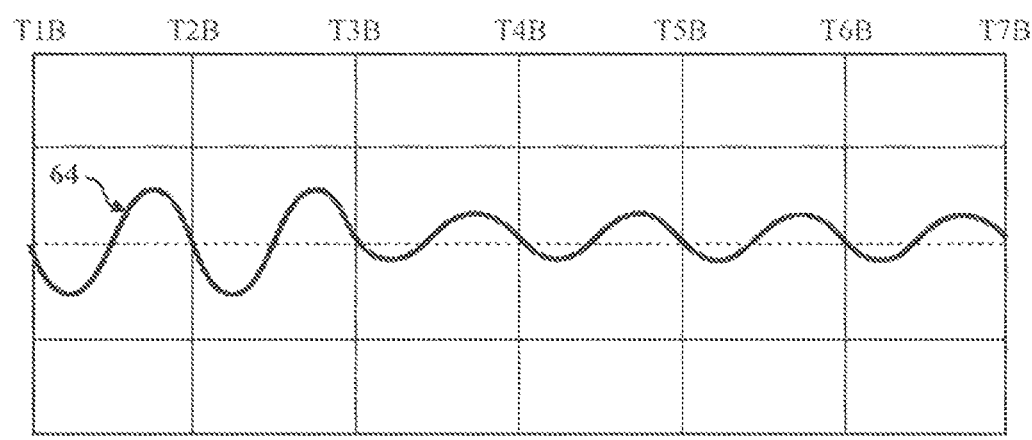
FIG. 12B is a graph depicting an alternate instance of the second receive signal of FIG. 11C, representing a metallic object brought nearby the detection system.
Figure 12C:
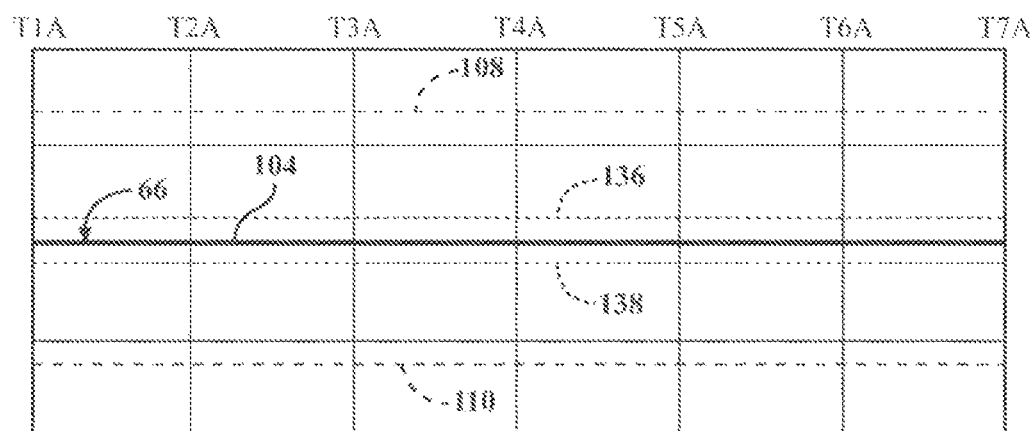
FIG. 12C is a graph depicting a waveform generated by the controller of FIG. 3 based on the first receive signal of FIG. 12A and the second receive signal of FIG. 12B, the waveform representing a metallic object brought nearby the detection system.

Referring now to FIGS. 12A-12C, another set of graphs are shown along a different common time scale delineated between seven equally-spaced time references T1B, T2B, T3B, T4B, TSB, T6B, and T7B. Here, the graphs respectively represent the first receive signal 62 in the first receive coil 52 (see FIG. 12A), the second receive signal 64 in the second receive coil 54 (see FIG. 12B), and the waveform 66 generated by the controller 58 based on the receive signals 62, 64 (see FIG. 12C) during an operating condition of the detection system 48 wherein the waveform 66 has a baseline 104 condition corresponding to a transient interaction of a metallic object with the magnetic field which affects both receive signals 62, 64 simultaneously.

The transient metallic object described above and represented in the graphs depicted in FIGS. 12A-12C could be a portable steel IV pole used to hang fluid bags (not shown, but generally known in the art). Here, the IV pole is placed nearby the detection system 48, but outside a footprint of the mobile cart 30, at the third time reference T3B and, thus, begins to affect the amplitude of the receive signals 62, 64 simultaneously at the third time reference T3B (compare amplitude in FIGS. 12A and 12B). However, because the steel IV pole affects the receive signals 62, 64 simultaneously and equally, no differential occurs between the receive signals 62, 64 and, thus, the resulting waveform 66 generated by the controller 58 is shown as a substantially flat line from the first time reference T1B to the seventh time reference T7B so as to indicate that the baseline 104 remains substantially constant over time (see FIG. 12C). Put differently, the baseline 104 has zero amplitude (no AC component) during this operating condition. Thus, simultaneous changes occurring in the receive signals 62, 64 are not noticed in the waveform 66 when combined by the controller 58, thereby contributing to enhanced sensitivity and helping to prevent inadvertent and inaccurate activation of the detection indicator 50 in response to transient metallic objects passing nearby the detection system 48.

Figure 13A:
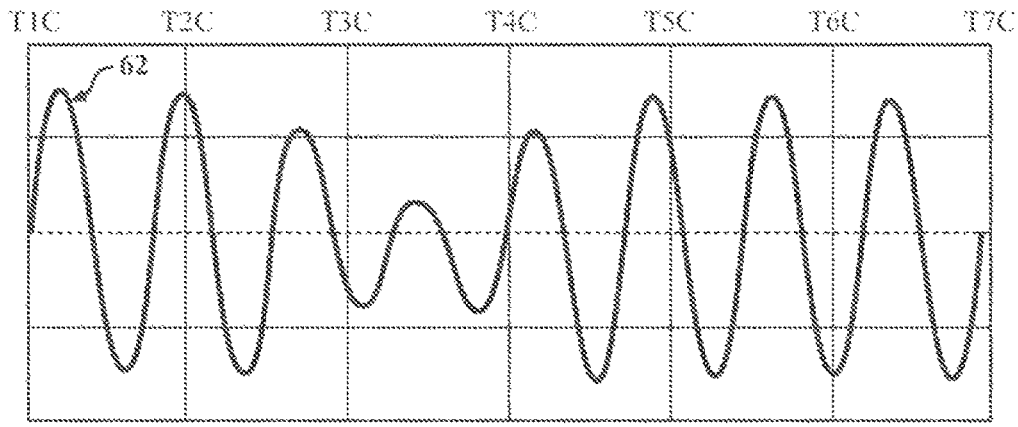
FIG. 13A is a graph depicting another alternate instance of the first receive signal of FIG. 11B, representing a metallic object passing through the coils of the detection system of FIG. 3.
Figure 13B:
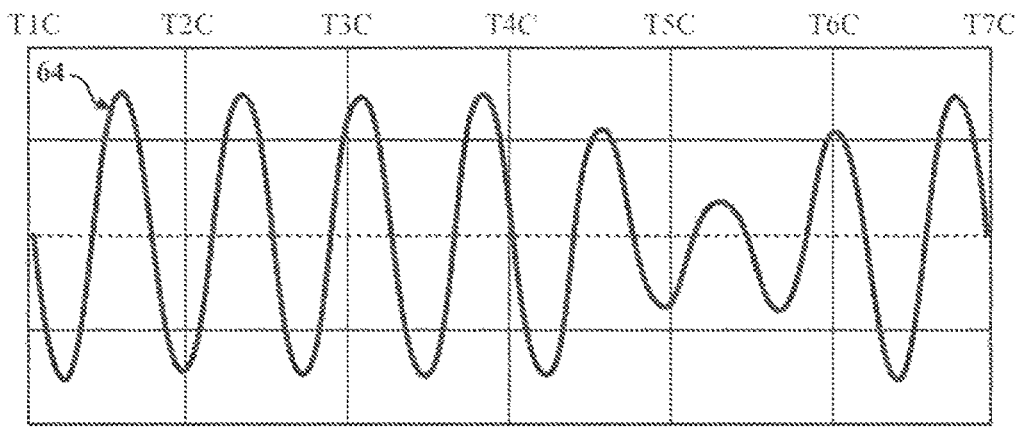
FIG. 13B is a graph depicting another alternate instance of the second receive signal of FIG. 11C, representing a metallic object passing through the coils of the detection system of FIG. 3.
Figure 13C:
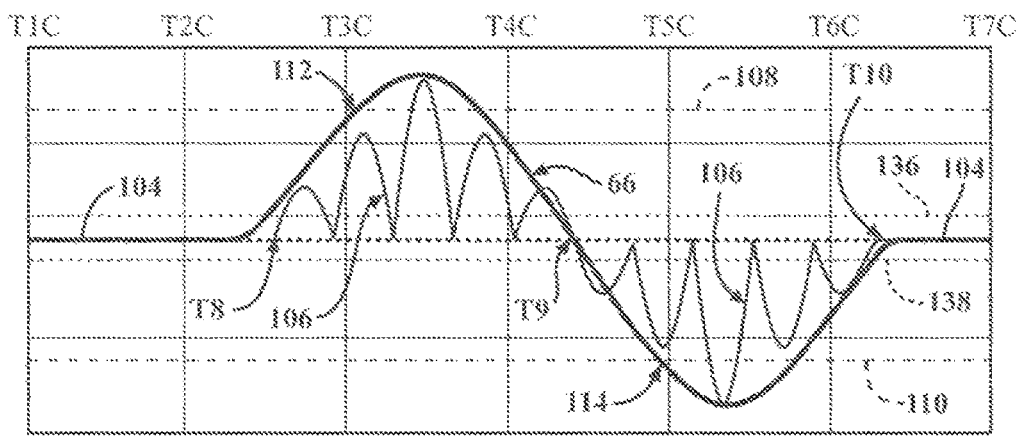
FIG. 13C is a graph depicting a waveform generated by the controller of FIG. 3 based on the first receive signal of FIG. 13A and the second receive signal of FIG. 13B, the waveform representing a metallic object passing through the coils of the detection system of FIG. 3.

Referring now to FIGS. 13A-13C, another set of graphs are shown along a different common time scale delineated between seven equally-spaced time references T1C, T2C, T3C, T4C, T5C, T6C, and T7C. Here, the graphs respectively represent the first receive signal 62 in the first receive coil 52 (see FIG. 13A), the second receive signal 64 in the second receive coil 54 (see FIG. 13B), and the waveform 66 generated by the controller 58 based on the receive signals 62, 64 (see FIG. 13C) during an operating condition of the detection system 48 wherein a metallic object passes through the opening 44 of the medical waste container 42. As shown in FIG. 13C, in one embodiment, the receive signals 62, 64 are combined arithmetically into a single combined signal, generally indicated at 106, resulting from the absolute value of the second receive signal 64 subtracted from the absolute value of the first receive signal 62. Here, the controller 58 can generate the waveform 66 shown in FIG. 13C by enveloping the combined signal 106. It will be appreciated that enveloping of the combined signal 106 can be effected in a number of different ways, such as with rectifiers, inverters, and/or other circuits or modules. More specifically, the waveform 66 can be generated using any suitable type of integrating circuit sufficient to determine the area under the time domain curve of the combined signal 106.

The metallic object described above and represented in the graphs depicted in FIGS. 13A-13C could be a reusable surgical tool manufactured from stainless steel (not shown, but generally known in the art). Here, the surgical tool passes consecutively through the first receive coil 52, the transmit coil 56, and then the second receive coil 54. In this representative embodiment, the surgical tool begins to affect the amplitude of the first receive signal 62 between the second time reference T2C and the third time reference T3C as the surgical tool approaches the first receive coil 52, and subsequently begins to affect the amplitude of the second receive signal 64 between the fourth time reference T4C and the fifth time reference T5C as the surgical tool approaches the second receive coil 54, having passed through the first receive coil 52 and the transmit coil 56. Thus, the first receive signal 62 changes before the second receive signal 64 changes (compare FIGS. 13A and 13B), which causes the resulting waveform 66 to move from the baseline 104 in response. Specifically, as shown in FIG. 13C, the waveform 66 begins to move from the baseline 104 after the second time reference T2C and increases in amplitude from the baseline 104 as the surgical tool approaches the first receive coil 52, and subsequently decreases in amplitude back towards the baseline 104 after the surgical tool passes through the first receive coil 52 and approaches the transmit coil 56.

As shown in FIG. 13C, the waveform 66 continues to decrease in amplitude as the surgical tool passes through the transmit coil 56 and approaches the second receive coil 54. The waveform 66 subsequently increases in amplitude back towards the baseline 104 after the surgical tool passes through the second receive coil 54. It will be appreciated that additional information about the surgical tool's interaction with the metal detection system can be determined. For example, the time when the surgical tool interacts equally with both receive signals 62, 64 is when the combined signal 106 intersects the baseline 104 at time T9. This typically would be very close to the time when the object is at the center plane formed by the transmit coil 56. In addition, the time it takes the object to travel through the magnetic field would be when the combined signal 106 first deviates from its baseline at time T8, passing the midpoint at time T9 and then leaving the magnetic field at time point T10. In some embodiments, various times related to the combined signal 106 or the waveform 66 can be analyzed in order to improve the determination of detection events, count detection events or set detection indicator 50.

The controller 58 analyzes the waveform 66 with respect to a first detection threshold 108 and also to a second detection threshold 110 opposite to the first detection threshold 108, with the baseline 104 being between the first detection threshold 108 and the second detection threshold 110. Here, the controller 58 is configured to activate the detection indicator 50 in response to the metal surgical tool passing through the coils 52, 54, 56, based on the waveform 66 exceeding the first detection threshold 108 at a first time 112 and exceeding the second detection threshold 110 at a subsequent second time 114.

Figure 11D:
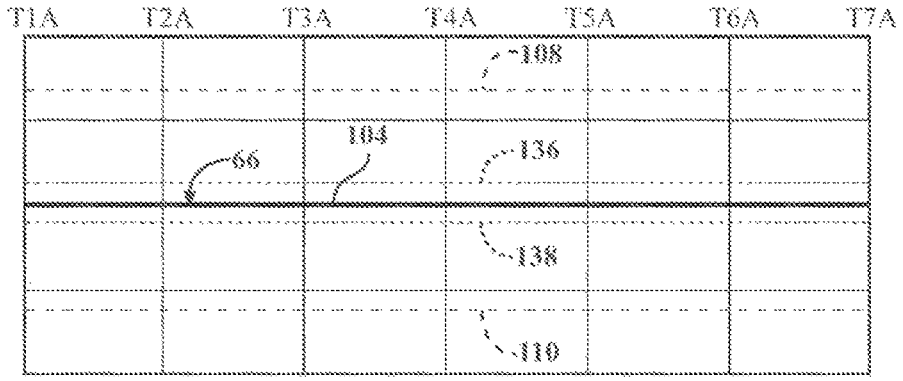
FIG. 11D is a graph depicting a waveform generated by the controller of FIG. 3 based on the first receive signal of FIG. 11B and the second receive signal of FIG. 11C, representing an absence of metallic objects adjacent to the detection system.

During an absence of interaction of metallic objects with the magnetic field, as shown in FIG. 11D, the receive signals 62, 64 result directly from the transmit signal 60, and are substantially equal and opposite to each other because of the electrical balancing and physical symmetry of the coils 52, 54, 56 of the detection system 48, as noted above. More specifically, flux from the magnetic field is advantageously distributed evenly between the receive coils 52, 54 and, thus, the receive signals 62, 64 are substantially equal and opposite to each other when there are no magnetic objects interacting with the magnetic field generated by the transmit coil 56. However, when a differential occurs between the receive signals 62, 64, the waveform 66 correspondingly moves from the baseline 104, as shown, in one example, in FIG. 13C. Thus, interaction of metallic objects with the magnetic field generated by the transmit coil 56 is reflected in the receive signals 62, 64. Here, the controller 58 analyzes movement of the waveform 66 from the baseline 104 and with respect to the detection thresholds 108, 110 to detect passage of metallic objects through the opening 44 of the medical waste container 42.

It will be appreciated that objects can interact with the magnetic field generated by the transmit coil 56 in a number of different ways. In particular, material properties and physical characteristics of the object affect how the receive signals 62, 64 change in response to interaction with the magnetic field. As such, objects of different sizes, shapes, and material compositions passing through the coils 52, 54, 56 can affect movement of the waveform 66 from the baseline 104 in correspondingly different ways.

By way of example, if a non-conductive and magnetic material (ferromagnetic or paramagnetic), such as a ferrite tile, interacts with the magnetic field generated by the transmit coil 56, the distribution of magnetic flux from the transmit coil 56 and around the receive coils 52, 54 will be altered because of a change in the total permeability in the volume adjacent the coils 52, 54, 56. Similarly, if a conductive and magnetic material (ferromagnetic, paramagnetic, or diamagnetic), such as a metal needle, interacts with the magnetic field generated by the transmit coil 56, eddy current will be induced in the object which, in turn, creates a secondary magnetic field in opposition to the magnetic field generated by the transmit coil 56.

It will be appreciated that the specific configuration of the secondary magnetic field generated as a result of eddy currents depends on physical characteristics of the conductive magnetic object, such as conductivity, permeability, size, shape, and orientation. Conductive materials with high relative permeability (for example: steel) will tend to increase the total permeability in the volume adjacent the coils 52, 54, 56 because the secondary magnetic field created by eddy currents within the material is generally insufficient to counteract the magnetic field generated by the transmit coil 56. However, highly-conductive materials with low relative permeability (for example: copper or aluminum) will tend to decrease the total permeability in the volume adjacent the coils 52, 54, 56 because the secondary magnetic field created by eddy currents within the highly-conductive material tends to repel the magnetic field generated by the transmit coil 56. Further, moderately-conductive materials that have low relative permeability (for example: tin, lead, titanium, and certain types of stainless steel) will have a relatively small effect on the total permeability in the volume adjacent the coils 52, 54, 56 because the secondary magnetic field results from relatively small eddy currents within the moderately-conductive material.

In the representative operating condition described above, the passage of the stainless steel surgical tool through the coils 52, 54, 56 causes a successive change in the amplitude of the receive signals 62, 64 which, in turn, causes the waveform 66 to move from the baseline 104. Here, while the amplitude of each of the receive signals 62, 64 is reduced when the steel surgical tool approaches the respective receive coil 52, 44, those having ordinary skill in the art will appreciate that differential imbalance between the receive signals 62, 64 can occur in other ways sufficient to move the waveform 66 from the baseline 104. By way of a non-limiting example, the receive signals 62, 64 could successively increase in amplitude, increase or decrease in frequency, and/or shift in phase in response to certain metallic objects passing through the coils 52, 54.

As such, it will be appreciated that the waveform 66 generated by the controller 58 could move from the baseline 104 in response to any suitable predetermined type of differential change occurring between the receive signals 62, 64. Moreover, it will be appreciated that different types of materials effect correspondingly different differential changes in the receive signals 62, 64 when interacting with the magnetic field generated by the transmit coil 56, based on size, shape, conductivity, permeability, and the like, as noted above. Thus, the detection system 48 could be configured so as to recognize certain materials or objects based at least partially upon characteristic differential changes occurring in the amplitude, frequency, and/or phase of the receive signals 62, 64 and/or the waveform 66. As such, the controller 58 could further be configured to operate differently depending on the particular object recognized. By way of a non-limiting example, the controller 58 could be configured so as not to activate the detection indicator 50, or to activate the detection indicator 50 in a different way (such as with a distinct audible tone or light activation/flash rate) when certain recognized metallic objects pass through the coils 52, 54, 56, such as a commonly discarded metallic objects (for example: a foil wrapper, grounding pad, an instrumentation tip, or a sensor cable).

Figure 14A:
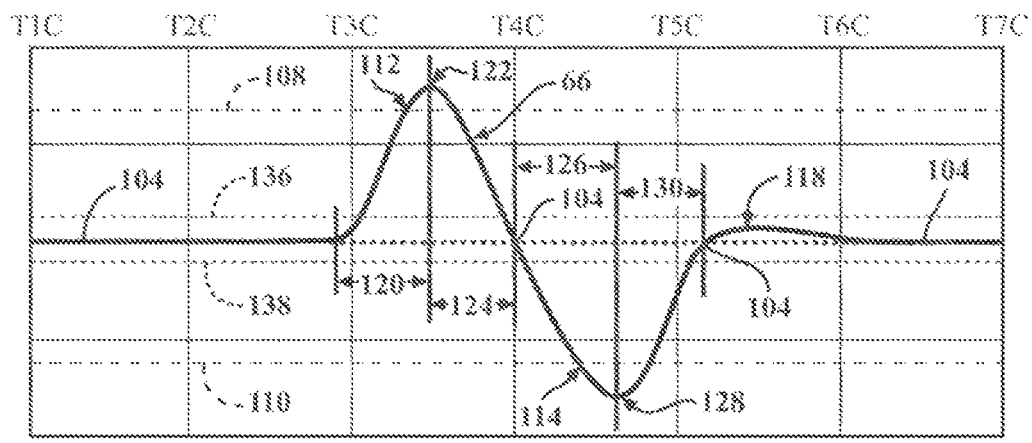
FIG. 14A is an enlarged version of the graph of FIG. 13C showing additional detail and depicting a waveform generated in response to a metallic object passing through the coils of the detection system, the metallic object having high relative permeability.

Referring now to FIG. 14A, an alternate and enlarged version of the graph depicted in FIG. 13C is shown with additional detail. The graph shown in FIG. 14A is likewise shown along a time scale delineated between seven equally-spaced time references T1C, T2C, T3C, T4C, T5C, T6C, and T7C. Here too, the graph represents the waveform 66 generated by the controller 58 based on the receive signals 62, 64 during an operating condition of the detection system 48 when a metallic object, such as the stainless steel surgical tool, passes into the opening 44 of the medical waste container 42. In this operating condition of the detection system 48, the waveform 66 exceeds the first detection threshold 108 at the first time 112, and subsequently exceeds the second detection threshold 110 at the second time 114.

Figure 16:
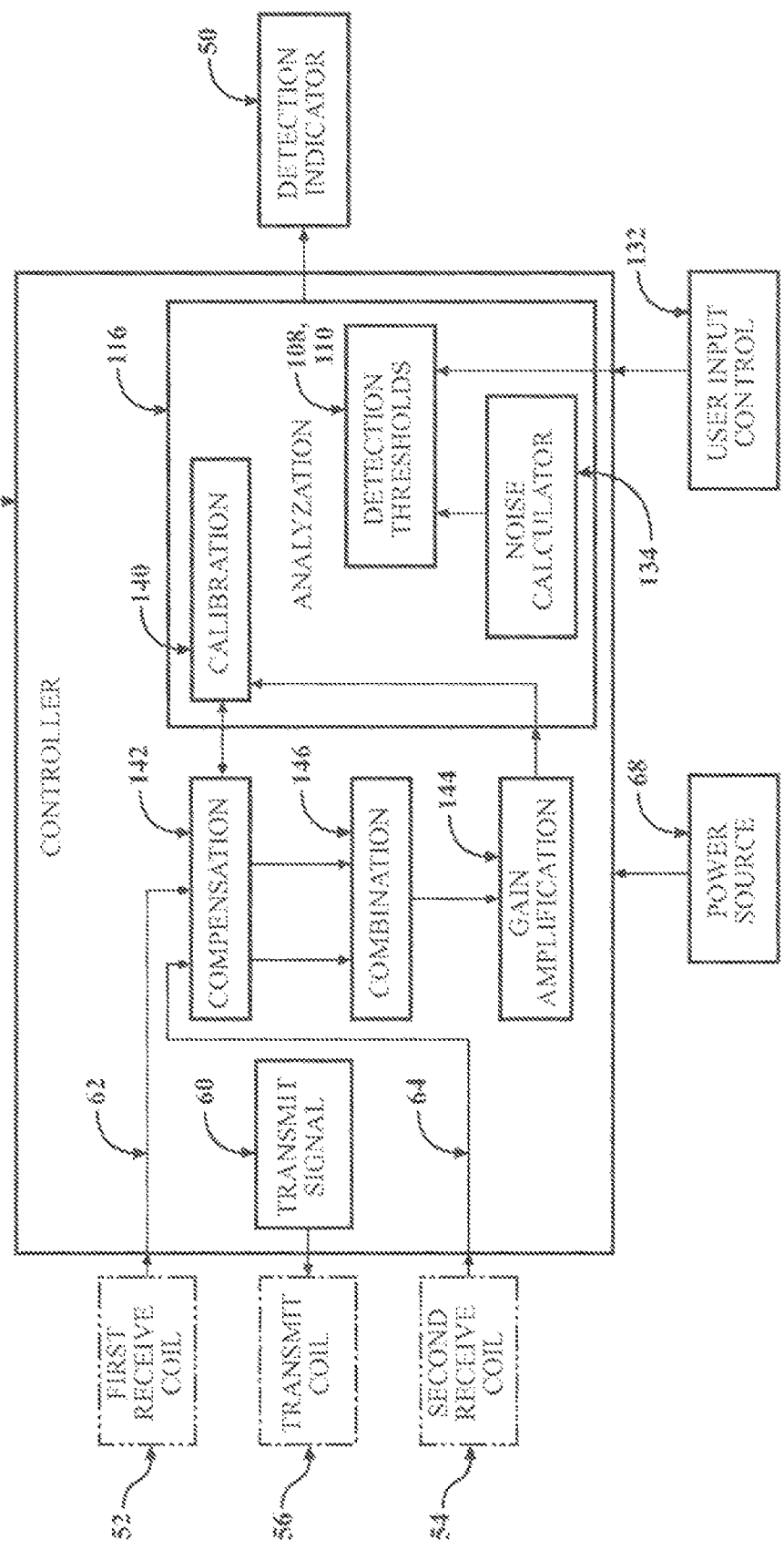
FIG. 16 is a schematic representation of the detection system of FIG. 3, according to one embodiment.

In one embodiment, the controller 58 comprises an analyzation circuit 116 (see FIG. 16) which is configured to monitor the waveform 66 with respect to the baseline 104 and the detection thresholds 108, 110 so as to detect the passage of metallic objects into the opening 44 of the medical waste container 42. In one embodiment, the analyzation circuit 116 (see FIG. 16) of the controller 58 is configured to activate the detection indicator 50 in response to the waveform 66 exceeding the first detection threshold 108 at the first time 112, and exceeding the second detection threshold 110 at the second time 114. In one embodiment, the analyzation circuit 116 (see FIG. 16) of the controller 58 is configured to activate the detection indicator 50 in response to the waveform 66 being between the detection thresholds 108, 110 at a subsequent third time 118.

As will be appreciated from the subsequent description below, the detection thresholds 108, 110 could be defined in any suitable way and with any suitable orientation with respect to each other sufficient to enable the controller 58 to detect movement of the waveform 66 successively across each of the detection thresholds 108, 110. By way of non-limiting example, the waveform 66 depicted in FIG. 14A could represent a steel object passing through the coils 52, 54, 56 into the opening 44 of the medical waste container 42. Here, the second detection threshold 110 is equal in terms of amplitude to the first detection threshold 108, and is defined as being "below" the first detection threshold 108 and the baseline 104 of the waveform 66. Conversely, the waveform 66 depicted in FIG. 14B could represent an aluminum object passing through the coils 52, 54, 56 into the opening 44 of the medical waste container 42. Here, the second detection threshold 110 is equal in terms of amplitude to the first detection threshold 108, but is defined as being "above" the first detection threshold 108 and the baseline 104 of the waveform 66. Thus, the detection thresholds 108, 110 can be defined in any suitable way with respect to each other with the waveform 66 exceeding the first detection threshold 108 before the second detection threshold 110 when a metallic object passes into the opening 44 of the medical waste container 42.

As noted above, the operating condition of the detection system 48 depicted in FIG. 14A represents a stainless steel object passing into the opening 44 of the medical waste container 42, wherein the waveform 66 moves towards the first detection threshold 108 with increasing amplitude as the stainless steel object approaches the first coil 52. Here, the controller 58 is configured to activate the detection indicator 50 based on the waveform 66 successively: increasing amplitude over a first period 120 from the baseline 104 to beyond the first detection threshold 108 to define a first detection event point 122; decreasing amplitude over a second period 124 from the first detection event point 122 to the baseline 104, and decreasing amplitude over a third period 126 from the baseline 104 to beyond the second detection threshold 110 to define a second detection event point 128. In one embodiment, the first and second periods 120, 124 are of substantially equal duration. In other embodiments, the first and second periods 120, 124 are different durations. These first and second periods 120, 124 are proportional to the amount of time a metallic item first enters the magnetic field until it reaches a center plane defined by the transmit coil 56.

In another embodiment, the analyzation circuit 116 of the controller 58 is configured to activate the detection indicator 50 based on the waveform 66 increasing amplitude over a fourth period 130 from the second detection event point 128 to the baseline 104. Here, because a predetermined amount of time must elapse before the waveform 66 will settle to the baseline 104, the analyzation circuit 116 of the controller 58 may alternatively be configured to activate the detection indicator 50 based on the waveform 66 increasing amplitude over the fourth period 130 from the second detection event point 128 to within a predetermined threshold with respect to the baseline 104, such as within 15% of the amplitude of the waveform 66 occurring at the second detection event point 128. In one embodiment, the analyzation circuit 116 (see FIG. 16) of the controller 58 is configured to activate the detection indicator 50 in response to the waveform 66 exceeding the first detection threshold 108 and the second detection threshold 110 at the second time 114. It will be appreciated that the controller 58 can activate the detection indicator 50 based on the thresholds 108, 110 and irrespective of the periods described above.

Once the first detection threshold 108 is exceeded at the first time 112, the controller 58 marks the beginning of a detection event. Once the first detection event point 122 is reached, an actual detection event will cause the waveform 66 to pass back through the baseline 104 to the second detection event point 128 after the second threshold 110 is exceeded at the second time 114, as noted above. The amplitude of the waveform 66 at the second detection event point 128 should be at least 100% of the second threshold 110, as well as at least 20% of the opposing amplitude occurring at the first detection event point 122. Here, if the amplitude of the waveform 66 does not exceed the second threshold 110 at the second time 114, then no detection event occurs because the metallic object did not pass through both of the receive coils 52, 54. Similarly, if the amplitude of the waveform 66 exceeds the second threshold 110 at the second time 114, but the amplitude occurring at the second detection event point 128 is less than 20% of the opposing amplitude occurring at the first detection event point 122, then no detection event occurs because the metallic object did not pass through both of the receive coils 52, 54.

Figure 14B:
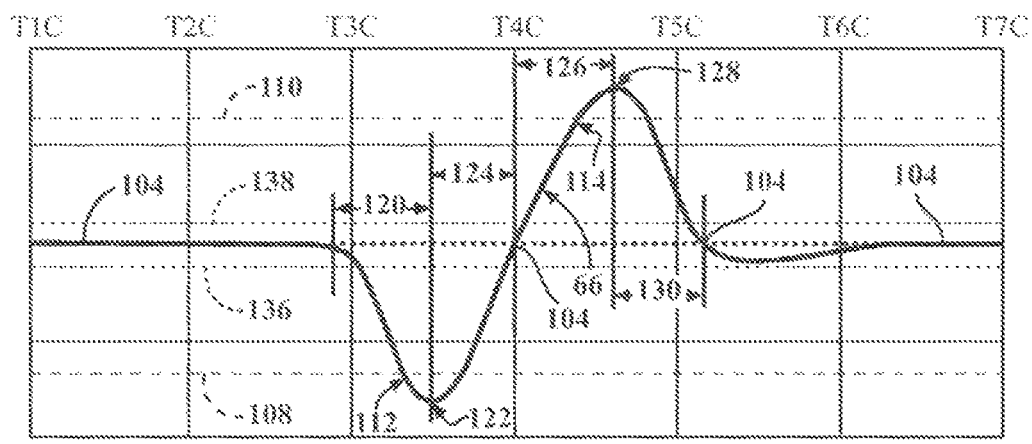
FIG. 14B is an alternate version of the graph of FIG. 14A depicting a waveform generated in response to a metallic object passing through the coils of the detection system, the metallic objecting having low relative permeability.

As noted above, the operating condition of the detection system 48 depicted in FIG. 14B represents an aluminum object passing into the opening 44 of the medical waste container 42, wherein the waveform 66 moves towards the first detection threshold 108 with decreasing amplitude as the aluminum object approaches the first coil 52. Here, the controller 58 is configured to activate the detection indicator 50 based on the waveform 66 successively: decreasing amplitude over the first period 120 from the baseline 104 to beyond the first detection threshold 108 to define the first detection event point 122; increasing amplitude over the second period 124 from the first detection event point 122 to the baseline 104; and increasing amplitude over the third period 126 from the baseline 104 to beyond the second detection threshold 110 to define the second detection event point 128. In one embodiment, the controller 58 is configured to activate the detection indicator 50 based on the waveform 66 decreasing amplitude over the fourth period 130 from the second detection event point 128 to the baseline 104.

The detection system 48 is advantageously configured so as not to activate the detection indicator 50 when a metallic object is subsequently removed from the medical waste container 42, which can be irritating to users. However, as noted above, different types of metallic objects passing into the opening 44 of the medical waste container 42 interact with the magnetic field generated by the transmit coil 56 in different ways. By way of non-limiting example, while the waveform 66 depicted in FIG. 14A represents a steel object passing into the medical waste container 42 and the waveform 66 depicted in FIG. 14B represents an aluminum object passing into the medical waste container 42, the waveform 66 depicted in FIG. 14B could alternatively represent a steel object being removed from the medical waste container 42. More specifically, movement of a steel object out of the medical waste container 42 could result in a waveform 66 which is similar to a waveform 66 generated as a result of an aluminum object moving into the medical waste container 42.

In order to prevent activation of the detection indicator 50 during an operating condition where a metallic object is removed from the medical waste container 42, in one embodiment, the analyzation circuit 116 of the controller 58 is configured to simultaneously analyze the receive signals 62, 64 as well as the waveform 66 generated from the receive signals 62, 64. The controller 58 is configured to activate the detection indicator 50 based on predetermined changes occurring in the first receive signal 62 of the first receive coil 52 and subsequent predetermined changes occurring in the second receive signal 64 of the second receive coil 54, and based further on the waveform 66 exceeding the first detection threshold 108 at the first time 112 and exceeding the second detection threshold 110 at the subsequent second time 114. Thus, a change occurring in the second receive signal 64 before the first receive signal 62 represents removal of a metallic object irrespective of the specific physical configuration or material properties of the object, and the controller 58 will not activate the detection indicator 50 in response because the first receive coil 52 is spaced above the second receive coil 54 such that objects dropped into the opening 44 of the medical waste container 42 pass through the first receive coil 52 before passing through the second receive coil 54 (see FIGS. 3, 7, and 8).

During certain operating conditions of the detection system 48, transient metallic objects passing nearby the coils 52, 54, 56 can interact with the magnetic field generated by the transmit coil 56 such that the waveform 66 at least partially moves from the baseline 104 in response. Specifically, where transient metallic objects nearby the detection system 48 move unevenly with respect to the arrangement of the coils 52, 54, 56, the resulting waveform 66 could move from the baseline 104 despite the filtering afforded by the electrical and physical balancing described above.

Figure 15A:
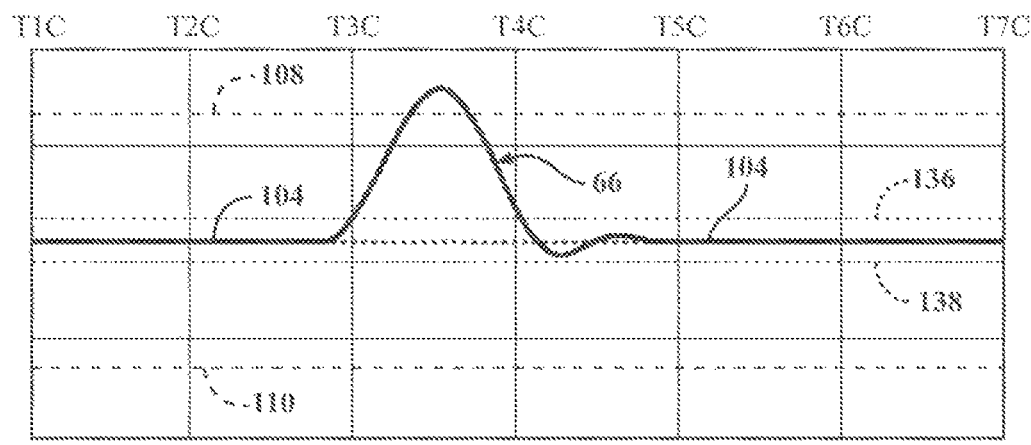
FIG. 15A is a graph depicting a waveform generated by the controller of FIG. 3, representing a metallic object passing nearby the first receive coil of the detection system.
Figure 15B:
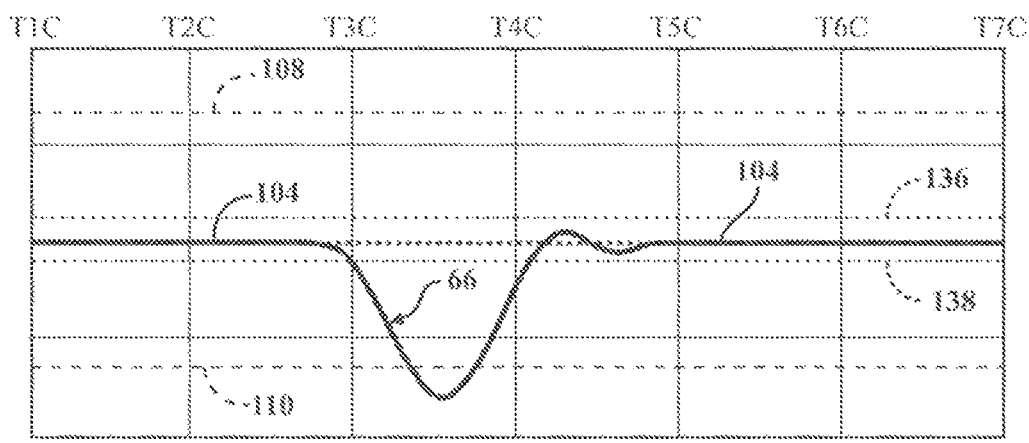
FIG. 15B is a graph depicting a waveform generated by the controller of FIG. 3, representing a metallic object passing nearby the second receive coil of the detection system.

Referring now to FIGS. 15A and 15B, graphs are shown depicting certain operating conditions of the detection system 48 where transient movement of a metallic object affects one of the receive signals 62, 64 enough to move the waveform 66 from the baseline 104 without passing through the coils 52, 54, 56. By way of non-limiting example, such a transient metallic object could be a wristwatch worn by a person walking nearby the mobile cart 30. The waveform 66 depicted in FIG. 15A would be generated if the wristwatch were positioned vertically closer to the first receive coil 52 than to the second receive coil 54. Here, the first receive signal 62 changes while the second receive signal 64 remains substantially unchanged. Similarly, the waveform 66 depicted in FIG. 15B would be generated if the wristwatch were positioned vertically closer to the second receive coil 54 than to the first receive coil 52. Here, the second receive signal 64 changes while the first receive signal 62 remains substantially unchanged.

Thus, transient metallic objects passing at least partially horizontally nearby the receive coils 52, 54 could cause a differential change between the receive signals 62, 64 sufficient to move the waveform 66 from the baseline 104. However, transient movement of this type does not result in a waveform 66 which is indicative of passage of a metallic object into the opening 44 of the medical waste container 42 because the waveform 66 will not successively exceed both of the detection thresholds 108, 110. Rather, the operating conditions described above will result in the analyzation circuit 116 of the controller 58 seeing only one of the detection thresholds 108, 110 exceeded, after which the waveform 66 will subsequently return to the baseline 104 as the metallic object moves away from the magnetic field.

Referring now to FIGS. 14A and 16-20, as noted above, the controller 58 activates the detection indicator 50 in response to the first and second detection thresholds 108, 110 being successively exceeded. In one embodiment, the detection thresholds 108, 110 are adjustable by a user input control, shown generically at 132 (see also FIGS. 1 and 3). The user input control 132 is in electrical communication with the controller 58 and allows the user to manually adjust the sensitivity and/or operating mode of the detection system 48, as described in greater detail below. By way of non-limiting example, the user input control 132 could be realized as a rotary potentiometer employed to at least partially change the detection thresholds 108, 110 with respect to the baseline 104 of the waveform 66. However, it will be appreciated that the user input control 132 could be realized in a number of different ways and, thus, could be configured to communicate with or otherwise control the detection system 48 in any suitable way sufficient to effect user-manipulated adjustability and/or control. For instance, the user input control 132 could be implemented as inputs on a touch screen, physical buttons that activate switches, and the like. Moreover, it will be appreciated that the user input control 132 could serve other purposes, such as to silence the detection indicator 50.

In one embodiment, the controller 58 includes a noise calculator 134 configured to establish first and second noise boundaries 136, 138 based on prior minimum and maximum values of the waveform 66 received over a predetermined period of time (see FIG. 14A). The noise calculator 134 is employed to help determine the detection thresholds 108, 110 based at least partially on the set noise boundaries 136, 138, whereby subsequent movement of the waveform 66 from the baseline 104 that does not exceed the noise boundaries 136, 138 can be ignored or otherwise filtered out. Thus, changes in the waveform 66 below the noise boundaries 136, 138 can be considered noise, and certain changes in the waveform 66 above the noise boundaries 136, 138 can be used to determine the presence of metallic objects passing into the opening 44 of the medical waste container 42.

Here, the detection thresholds 108, 110 are established as a percentage of the noise boundaries 136, 138 greater than 100%. In one embodiment, the detection thresholds 108, 110 are established as 150% of the noise boundaries 136, 138. In another embodiment, the detection thresholds 108, 110 are established as 130% of the noise boundaries 136, 138. In another embodiment, the detection thresholds 108, 110 are established as 115% of the noise boundaries 136, 138. However, it will be appreciated that the detection thresholds 108, 110 can be set with respect to the noise boundaries 136, 138 in different ways, depending on the application and the operating environment in which the detection system 48 is utilized. Moreover, it will be appreciated that detection thresholds 108, 110 that are set as values approaching the noise boundaries 136, 138 can improve detection sensitivity and, thus, improve the detection system's 48 ability to detect metallic objects with relatively small magnetic field signatures.

Those having ordinary skill in the art will appreciate that the sensitivity of the detection system 48 is higher when the detection thresholds 108, 110 are set closer to the noise boundaries 136, 138. Moreover, it will be appreciated that the detection system 48 can be configured to adjust the noise boundaries 136, 138 over time to compensate for environmental changes occurring during use. Thus, in addition to initially setting the noise boundaries 136, 138 and the detection thresholds 108, 110, it is also advantageous to recalibrate the detection system 48 under certain operating conditions. To that end, in one embodiment, the analyzation circuit 116 of the controller 58 employs a calibration circuit 140. The calibration circuit 140 cooperates with a compensation circuit 142 and a gain amplification circuit 144 to monitor the waveform 66 over time for predetermined changes that indicate a need for recalibration so as to ensure detection accuracy.

As previously discussed, the detection system 48 is advantageously electrically balanced so as to effect enhanced sensitivity and detection accuracy. To that end, the controller 58 is employed to effect electrical balance of the coils 52, 54, 56. In one embodiment, the compensation circuit 142 is disposed in electrical communication with the first receive coil 52 and the second receive coil 54, and is configured to inductively balance the receive signals 62, 64 so as to minimize the baseline 104 of the waveform 66 such that subsequent changes from the baseline 104 can be accurately analyzed. Here, the compensation circuit 142 enhances the sensitivity of the detection system 48 by balancing the first receive signal 62 with the second receive signal 64 in terms of amplitude, frequency, and phase during an operating condition of the detection system 48 where no metallic objects interact with the magnetic field generated by the transmit coil 56. To that end, the compensation circuit 142 could utilize one or more microprocessors/microcontrollers configured to balance the receive signals 62, 64 when the detection system 48 is initialized, or as required during operation (not shown). As such, it will be appreciated that that enhanced sensitivity is promoted where the detection system 48 utilizes as little metallic material, components, structure, and the like as is practical. However, it will be appreciated that a certain amount of the detection system 48 necessarily involves the use of internal metallic components (such as the coils) to effect detection.

In one embodiment, the controller 58 employs a combination circuit 146 to combine the balanced receive signals 62, 64 into the waveform 66, To that end, in one embodiment, the combination circuit 146 is realized as a differential amplifier configured to combine the receive signals 62, 64 into the waveform 66 and further configured to attenuate the waveform 66 to the baseline 104 with zero amplitude. The controller 58 employs the gain amplification circuit 144 to amplify the waveform 66. Here, the gain amplification circuit 144 increases the sensitivity of the detection system 48 by amplifying the waveform 66 generated from the combined, balanced receive signals 62, 64 such that subsequent movement of the waveform 66 from the baseline 104 reflects imbalance between the receive signals 62, 64 caused by interaction of metallic objects with the magnetic field generated by the transmit coil 56.

Figure 17:
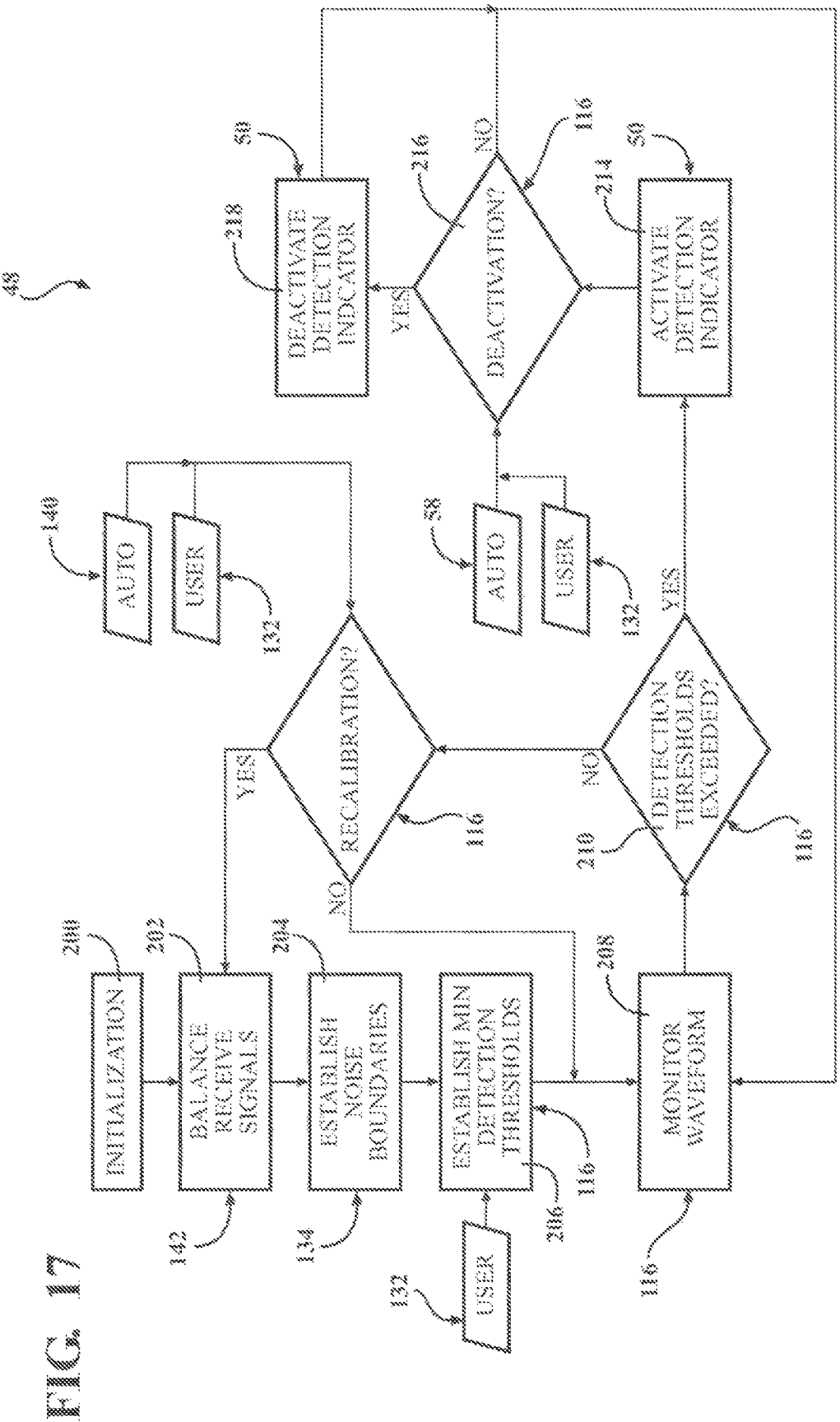
FIG. 17 is an exemplary logic map utilized by the detection system of FIG. 16, according to one embodiment.
Figure 18:
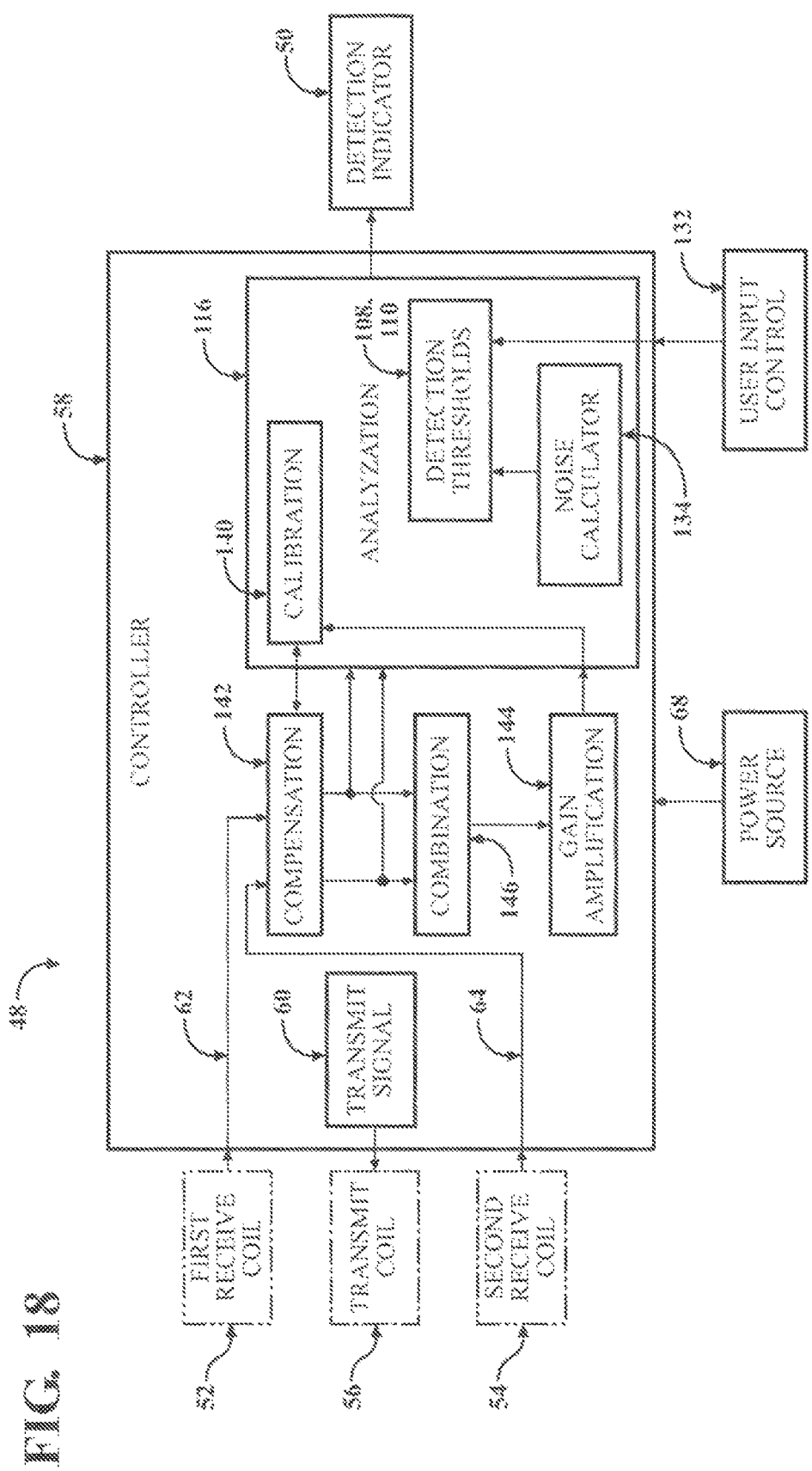
FIG. 18 is a schematic representation of the detection system of FIG. 3, according to another embodiment.
Figure 19:
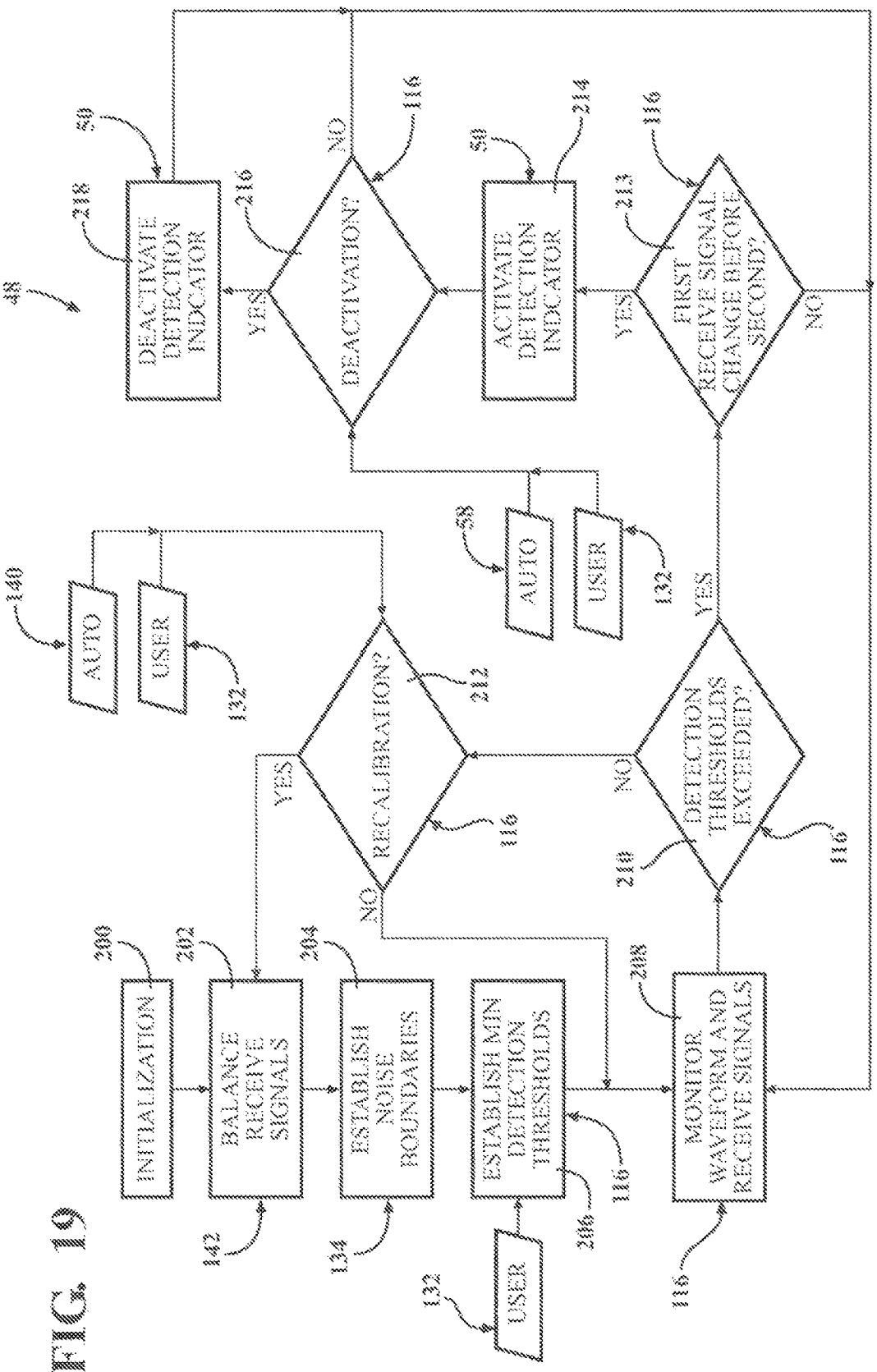
FIG. 19 is an exemplary logic map utilized by the detection system of FIG. 18, according to another embodiment.
Figure 20:
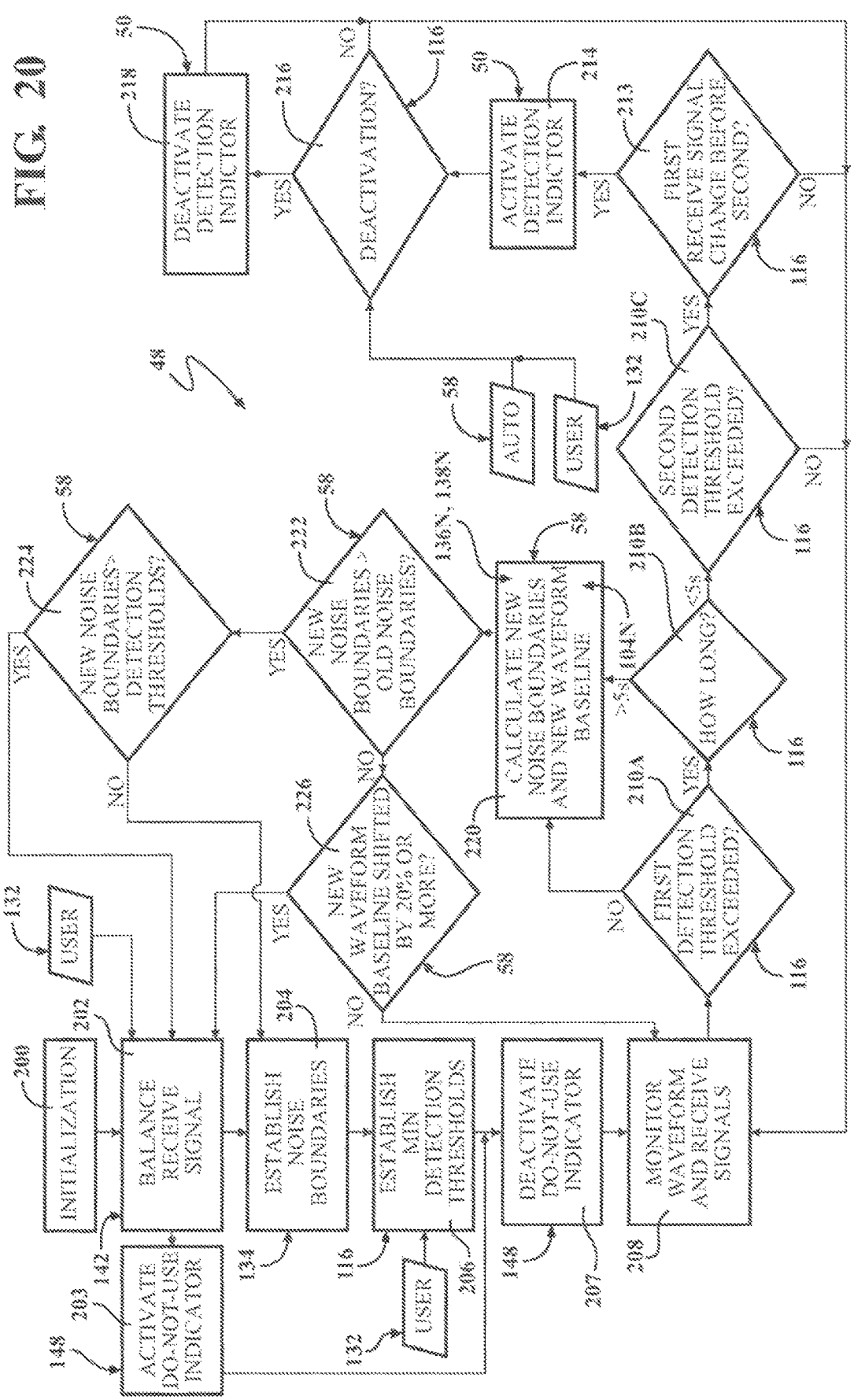
FIG. 20 is an alternate exemplary logic map utilized by the detection system of FIG. 18, according to another embodiment.

With reference now to the logic maps illustrated in FIGS. 17, 19 and 20, various logic steps employed by the detection system 48 are shown generally. Here, for the purposes of clarity and consistency, the steps are identified only with respect to the numeral with which they are introduced, beginning with numeral 200.

The detection system 48 is advantageously initialized in step 200 when there are no magnetic objects interacting with the magnetic field generated by the transmit coil 56. After initialization in step 200, the compensation circuit 142 balances the receive signals 62, 64 in step 202 and the noise calculator 134 establishes the noise boundaries 136, 138 based on the waveform 66 in step 204. Next, the detection thresholds 108, 110 are established in step 206 based on the noise boundaries 136, 138. Here, in step 206, the detection thresholds 108, 110 can also be manipulated by the user, such as via the user input control 132, as described above. Once the detection thresholds 108, 110 are established, the controller 58 then monitors the waveform 66 in step 208 for changes with respect to the baseline 104. Specifically, the analyzation circuit 116 of the controller 58 monitors the waveform 66 in step 208 for movement from the baseline 104 which exceeds the detection thresholds 108, 110, occurring in step 210. The controller 58 also simultaneously monitors for recalibration in step 212, which can be prompted automatically by the calibration circuit 140 or can be prompted manually by the user, such as via the user input control 132. If recalibration is prompted, in one embodiment, the controller 58 then re-balances the receive signals 62, 64 by returning to step 202, and re-establishes the noise boundaries 136, 138 in step 204 and the detection thresholds 108, 110 in step 206 before subsequently continuing to monitor the waveform 66 in step 208.

With continued reference to FIGS. 17 and 19, once the analyzation circuit 116 of the controller 58 determines that the detection thresholds 108, 110 have been exceed in step 210, the controller 58 subsequently activates the detection indicator 50 in step 214. In the embodiment illustrated in FIG. 19, the analyzation circuit 116 of the controller 58 also checks in step 213 to make sure the first receive signal 62 changed before the second receive signal 64 so as to differentiate between a metallic object being placed into the opening 44 of the medical waste container 42, and a metallic object being removed from the medical waste container 42.

As noted above, the detection indicator 50 could be implemented as an audible alarm and/or a visual alarm. By way of example, the detection indicator 50 could sound an audible alarm in step 214 whenever a metallic object passes into the opening 44 of the medical waste container 42 as determined in step 210, and the controller 58 could return to step 208 to continue to monitor the waveform 66 and re-sound the alarm in step 214 in response to a subsequent detection event determined in step 210.

Similarly, the detection indicator 50 could flash a light source in step 214 when a metallic object passes into the opening 44 of the medical waste container 34 as determined in step 210, and the controller 58 could return to step 208 to continue to monitor the waveform 66 in step 208 and re-illuminate the light source in step 214 in response to a subsequent detection event determined in step 210. Further, the detection indicator 50 could remain activated until deactivation is prompted in step 216 automatically by the controller 58 or prompted manually by the user, such as via the user input control 132, after which the detection indicator 50 could be deactivated in step 218. By way of example, the controller 58 could be configured to sound an alarm in step 214 via the detection indicator 50 until the metallic object is subsequently removed or until the user manipulates the user input control 132, in step 216.

The light source could be any light source suitable for indicating information to the user, such as a plurality of light emitting diodes, a plurality of multi-colored light emitting diodes, and the like. Additionally, the light source may be configured to generate visible light of different colors based on different information being conveyed to the user, such as red to indicate a detection event and green to indicate the absence of a detection event, but to show a ready status of the detection system 48. Moreover, the detection indicator 50 could employ light sources to indicate progress of a detection event as it occurs, such as by successively illuminating different light sources such as when the thresholds 108, 110 are exceeded, the detection event points 122, 128 are established, the times 112, 114, 118 occur, and the like. Moreover, the detection indicator 50 could include a counter to display the number of detection events which have occurred.

It will be appreciated that interaction of any metallic objects within the magnetic field generated by the transmit coil 56 may result in reduced sensitivity of the detection system 48 because the detection thresholds 108, 110 are established based on the noise boundaries 136, 138 of waveform 66. As noted above, the noise boundaries 136, 138 represent minimum and maximum values of deviation of waveform 66 from the baseline 104 over a set period of time. Moreover, any interaction of metallic objects with the magnetic field can cause the waveform 66 to move from the baseline 104, as described above. This movement causes the noise boundaries 136, 138 to increase which, in turn, causes a corresponding increase in the detection thresholds 108, 110 and, thus, a decrease in sensitivity. As such, it is advantageous for the control system 48 to compensate for decreased sensitivity caused by transient objects interacting with the magnetic field generated by the transmit coil 56, as well as movement of the waveform 66 caused by metallic objects passing through the coils 52, 54, 56. To that end, the calibration circuit 140 is configured to determine when to recalibrate. The time for recalibration may be based on as a predetermined amount of time passing, a detection event occurring, or a predetermined variation occurring in the waveform 66. It will be appreciated that recalibration can be effected in a number of different ways, such as by re-balancing the receive signals 62, 64, and/or by re-establishing the noise boundaries 136, 138 and/or the detection thresholds 108, 110 for an operating state.

As such, it will be appreciated that the detection system 48 could employ a number of different strategies to determine when to effect recalibration. By way of non-limiting example, a logic map depicting one embodiment of such a strategy is illustrated in FIG. 20. Here, the detection system 48 includes a do-not-use indicator 148 that is activated in step 203 whenever calibration or recalibration occurs in step 202, until the do-not-use indicator 148 is deactivated in step 207. It will be appreciated that activation of the do-not-use indicator 148 helps promote effective calibration due to user awareness, whereby the user can subsequently recalibrate via the user input control 132 if, for example, the user observes a metallic object being brought into close proximity with the detection system 48 while the do-not-use indicator 148 is activated. However, it will be appreciated that the do-not-use indicator 148 could be implemented in the detection system 48 in other ways, or could be omitted entirely.

With continued reference to FIG. 20, the controller 58 monitors the waveform 66 in step 208 with respect to the baseline 104 established during calibration, and determines if the first detection threshold 108 has been exceeded in step 210A. If the first detection threshold 108 is exceeded, the controller 58 determines if the first detection threshold 108 is exceeded for less than a predetermined amount of time in step 210B, such as 5 seconds, then the controller 58 subsequently checks in step 210O to see if the second detection threshold 110 has been exceeded to indicate a detection event, as described in greater detail above in connection to FIGS. 17 and 19. However, in this embodiment, if the first detection threshold 108 has not been exceeded, or has been exceeded for less than the predetermined amount of time, then the controller 58 subsequently calculates a new baseline 104N and new noise boundaries 136N, 138N in step 220 so as to determine if and how recalibration should occur.

In step 222, if the new noise boundaries 136N, 138N are larger than the previously established noise boundaries 136, 138, then the controller 58 compares the new noise boundaries 136N, 138N to the detection thresholds 108, 110 established during calibration in step 224. Here, if the new noise boundaries 136N, 138N are also larger than the detection thresholds 108, 110, then the controller 58 re-balances the receive signals 62, 64 in step 202 and re-establishes the noise boundaries 136, 138 in step 205 and the detection thresholds 108, 110 in step 206 before continuing to monitor the waveform 66 in step 208. However, if the new noise boundaries 136N, 138N are smaller than the detection thresholds 108, 110 in step 224, then the controller re-establishes the noise boundaries 136, 138 in step 204 and the detection thresholds 108, 110 in step 206 before continuing to monitor the waveform 66 in step 208.

If, however, the new noise boundaries 136N, 138N are smaller than the previously established noise boundaries 136, 138 in step 222, and if the controller 58 determines that the new baseline 104N has shifted by 20% or more in step 226 compared to the baseline 104 established previously during calibration, then the controller 58 re-balances the receive signals 62, 64 in step 202 and re-establishes the noise boundaries 136, 138 in step 204 and the detection thresholds 108, 110 in step 206 before continuing to monitor the waveform 66 in step 208. However, if the new baseline 104N has not shifted by 20% or more in step 226, then the controller 58 continues to monitor the waveform 66 in step 208. It will be appreciated that any one of the steps described above could be performed by the controller 58 in any suitable order, including sequentially, non-sequentially, and/or simultaneously. Moreover, it will be appreciated that the controller 58 could implement different strategies which employ steps organized in any suitable way. In the above example, the shift of 20% is provided as a non-limiting example wherein a different threshold of the shift percent can be used when appropriate.

As noted above, detection system 48 could be realized in a number of different ways and with a number of different configurations. Specifically, it will be appreciated that the controller 58, compensation circuit 142, combination circuit 146, gain amplification circuit 144, analyzation circuit 116, calibration circuit 140, and/or noise calculator 134 described above could be realized by any suitable number of discrete electrical components, modules, systems, sub-systems, processors, programs, and the like, that communicate or otherwise cooperate in any suitable way sufficient to effect detection of metallic objects passing through the coils 52, 54, 56, as described above. Moreover, it will be appreciated that one or more of the circuits and/or functions of the controller 58 described above could be realized as or otherwise carried out by software running on a processor. By way of non-limiting example, the controller 58 could comprise a processor running a signal conditioning algorithm which performs the functions of the compensation circuit 142, the combination circuit 146, and the gain amplification circuit 144 described above. Here too, the controller 58 could employ a common processor to carry out the functions of the analyzation circuit 116, as well as to generate the transmit signal 60.

In this way, the detection system 48 provides significantly increased sensitivity in detecting metallic objects dropped into the opening 44 of the medical waste container 42 while, at the same time, affording enhanced detection accuracy. Specifically, it will be appreciated that the physical and electrical balancing of the receive coils 52, 54 allows the controller 58 to monitor the waveform 66 for very slight variations from the baseline 104 while, at the same time, compensating for the presence of persistent and/or transient metallic objects positioned or moving nearby the detection system 48 and/or passing through the opening 44 of the medical waste container 42. Moreover, it will be appreciated that the detection system 48 affords significant opportunities for enhanced detection system 48 functionality, such as the ability to recognize certain metallic objects passing through the coils 52, 54, 56 and, thus, to differentiate between inadvertently disposed metallic objects and commonly discarded metallic objects.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

Embodiments of the disclosure can be described with reference to the following numbered clauses, with specific features laid out in the dependent clauses:

I. A detection system for detecting disposal of metallic objects into an opening of a medical waste container, said detection system comprising:
  a detection indicator for indicating passage of metallic objects through the opening of the medical waste container,
  a pair of receive coils and a transmit coil spaced between said receive coils, said coils being shaped for receiving waste therethrough adjacent to the opening of the medical waste container; and
  a controller in electrical communication with said coils, wherein said controller is configured to generate a transmit signal and communicate said transmit signal to said transmit coil such that said transmit coil generates a magnetic field based on said transmit signal, wherein said magnetic field induces voltage in each of said receive coils such that said receive coils each generate a receive signal received by said controller;
  wherein said controller is configured to generate a waveform based on both of said receive signals, wherein said waveform has a baseline condition corresponding to absence of interaction of metallic objects with said magnetic field;
  wherein said controller is configured to analyze said waveform with respect to a first detection threshold and a second detection threshold opposite to said first detection threshold with said baseline between said first detection threshold and said second detection threshold; and
  wherein said controller is configured to activate said detection indicator in response to metallic objects passing through said coils based on said waveform exceeding said first detection threshold at a first time and exceeding said second detection threshold at a subsequent second time.

II. The detection system as set forth in clause I, wherein said controller is configured to activate said detection indicator in response to said waveform being between said first detection threshold and said second detection threshold at a subsequent third time.

III. The detection system as set forth in any preceding clause, wherein said controller is configured to activate said detection indicator based on said waveform:

increasing amplitude over a first period from said baseline to beyond said first detection threshold to define a first detection event point, decreasing amplitude over a second period from said first detection event point to said baseline, and decreasing amplitude over a third period from said baseline to beyond said second detection threshold to define a second detection event point.

IV. The detection system as set forth in clause III, wherein said controller is configured to activate said detection indicator based on said waveform increasing amplitude over a fourth period from said second detection event point to said baseline.

V. The detection system as set forth in clause III, wherein said first and second periods are of substantially equal duration.

VI. The detection system as set forth in any preceding clause, wherein said baseline has zero amplitude.

VII. The detection system as set forth in any preceding clause, wherein said second detection threshold is equal in amplitude to said first detection threshold.

VIII. The detection system as set forth in any preceding clause, wherein said controller is configured to activate said detection indicator based on said waveform:

decreasing amplitude over a first period from said baseline to beyond said first detection threshold to define a first detection event point, increasing amplitude over a second period from said first detection event point to said baseline, and increasing amplitude over a third period from said baseline to beyond said second detection threshold to define a second detection event point.

IX. The detection system as set forth in clause VIII, wherein said controller is configured to activate said detection indicator based on said waveform decreasing amplitude over a fourth period from said second detection event point to said baseline.

X. The detection system as set forth in any preceding clause, wherein said controller includes a noise calculator configured to determine minimum values of said detection thresholds based on prior minimum and maximum values of said waveform received over a predetermined period of time when no metallic object interacts with said magnetic field.

XI. The detection system as set forth in clause X, wherein said detection thresholds are established as a percentage of said prior minimum and maximum values of said waveform noise greater than 100% of waveform noise.

XII. The detection system as set forth in any preceding clause, wherein said controller includes a compensation circuit configured to inductively balance said receive signals to minimize said baseline of said waveform.

XIII. The detection system as set forth in any preceding clause, wherein said controller includes a gain amplification circuit configured to amplify said waveform.

XIV. The detection system as set forth in any preceding clause, wherein said transmit signal is an oscillating voltage.

XV. The detection system as set forth in any preceding clause, wherein said transmit signal is sinusoidal.

XVI. The detection system as set forth in any preceding clause, wherein said magnetic field is an alternating magnetic field.

XVII. The detection system as set forth in any preceding clause, further including a power source for operating said detection system.

XVIII. The detection system as set forth in clause XVII, wherein said power source is a rechargeable battery.

XIX. The detection system as set forth in any preceding clause, further including a coil support frame supporting said coils, said coil support frame defining a passage through which the medical waste container is positionable to receive waste.

XX. The detection system as set forth in clause XIX, wherein said coil support frame has a profile defined by a round, oval, or polygonal shape.

XXI. The detection system as set forth in clause XIX, further including a mobile cart having a mount with said coil support frame operatively attached to said mount.

XXII. The detection system as set forth in any preceding clause, wherein each of said coils includes at least 25 turns of a conductive wire.

XXIII. The detection system as set forth in any preceding clause, wherein said coils are parallel.

XXIV. The detection system as set forth in any preceding clause, wherein said coils are co-axial.

XXV. The detection system as set forth in any preceding clause, wherein said transmit coil is spaced equidistantly between said receive coils.

XXVI. The detection system as set forth in any preceding clause, wherein said coils are spaced from each other at a predetermined distance between 20 mm and 80 mm.

XXVII. The detection system as set forth in clause XXVI, wherein said predetermined distance is between 40 mm and 60 mm.

XXVIII. The detection system as set forth in clause XXVI, wherein said predetermined distance is 50 mm.

XXIX The detection system as set forth in any preceding clause, wherein said coils have a profile defined by a round, oval, or polygonal shape.

XXX. The detection system as set forth in any preceding clause, wherein said coils have a common profile.

XXXI. The detection system as set forth in any preceding clause, wherein said coils have an irregular hexagonal profile.

XXXII. The detection system as set forth in any preceding clause, wherein said coils have a profile including at least one pair of parallel straight sides.

XXXII. The detection system as set forth in any preceding clause, wherein said first detection threshold and said second detection threshold are adjustable by a user input control.

XXXIV. The detection system as set forth in any preceding clause, wherein said detection indicator includes at least one of an audible and a visual indicator.

XXXV. The detection system as set forth in any preceding clause, further including a coil support frame supporting each of said receive coils and said transmit coil.

XXXVI. The detection system as set forth in clause XXXV, further including a mount for supporting said coil support frame, and a base coupled to said mount for concurrent movement.

XXXVII. The detection system as set forth in clause XXXVI, further including an isolation mechanism interposed between said mount and said coil support frame to isolate said coil support frame from external force acting on said mount.

XXXVIII. The detection system as set forth in clause XXXVII, wherein said isolation mechanism comprises a resilient member operatively attached to said mount and to said coil support frame.

XXXIX. The detection system as set forth in any preceding clause, further comprising a faraday shield configured to shield said receive coils from external electrical fields.

XL. The detection system as set forth in any preceding clause, further comprising a field shaping arrangement configured to direct magnetic fields generated by said transmit coil towards the opening of the medical waste container.

XLI. A detection system for detecting disposal of metallic objects into an opening of a medical waste container, said detection system comprising:
a detection indicator for indicating passage of metallic objects through the opening of the medical waste container;
a first receive coil, a second receive coil, and a transmit coil spaced between said receive coils, said coils being shaped for receiving waste therethrough adjacent to the opening of the medical waste container; and
a controller in electrical communication with said coils, wherein said controller is configured to generate a transmit signal and communicate said transmit signal to said transmit coil such that said transmit coil generates a magnetic field based on said transmit signal, wherein said magnetic field induces voltage in each of said receive coils such that said first receive coil generates a first receive signal and said second receive coil generates a second receive signal with both of said receive signals received by said controller;
wherein said controller is configured to generate a waveform based on both of said receive signals, wherein said waveform has a baseline condition corresponding to absence of interaction of metallic objects with said magnetic field;
wherein said controller is configured to analyze said waveform with respect to a first detection threshold and a second detection threshold opposite to said first detection threshold with said baseline between said first detection threshold and said second detection threshold; and
wherein said controller is configured to simultaneously analyze said receive signals and said waveform and is further configured to activate said detection indicator in response to metallic objects passing through said coils based on predetermined changes occurring in said first receive signal and subsequent predetermined changes occurring in said second receive signal, and based on said waveform exceeding said first detection threshold at a first time and exceeding said second detection threshold at a subsequent second time.

XLII. The detection system as set forth in clause XLI, wherein said first receive coil is spaced above said second receive coil such that objects dropped into the opening of the medical waste container pass through said first receive coil before passing through said second receive coil.

XLIII. The detection system as set forth in clause XLI, wherein said controller is configured to activate said detection indicator based on predetermined changes occurring in said receive signals and subsequently based on said waveform exceeding said detection thresholds.

XLIV. The detection system as set forth in clause XLI, wherein said controller is configured to activate said detection indicator based on said waveform exceeding said detection thresholds and subsequently based on predetermined changes occurring in said receive signals.

XLV. A detection system for detecting disposal of metallic objects into an opening of a medical waste container, said detection system comprising:
a detection indicator for indicating passage of metallic objects through the opening of the medical waste container;
a pair of receive coils and a transmit coil spaced between said receive coils, said coils being shaped for receiving waste therethrough adjacent to the opening of the medical waste container;
a coil support frame supporting each of said receive coils and said transmit coil;
a mount for supporting said coil support frame;
a base coupled to said mount for concurrent movement; and
an isolation mechanism interposed between said mount and said coil support frame to isolate said coil support frame from external force acting on said mount.

XLVI. The detection system as set forth in clause XLV, further comprising a controller in electrical communication with said coils, wherein said controller is configured to generate a transmit signal and communicate said transmit signal to said transmit coil such that said transmit coil generates a magnetic field based on said transmit signal, wherein said magnetic field induces voltage in each of said receive coils such that said receive coils each generate a receive signal received by said controller.

XLVII. The detection system as set forth in clause XLVI, wherein said controller is configured to generate a waveform based on both of said receive signals, and wherein said waveform has a baseline condition corresponding to absence of interaction of metallic objects with said magnetic field.

XLVIII. The detection system as set forth in clause XLVII, wherein said controller is configured to analyze said waveform with respect to a first detection threshold and a second detection threshold opposite to said first detection threshold with said baseline between said first detection threshold and said second detection threshold.

XLIX. The detection system as set forth in clause XLVII, wherein said controller is configured to activate said detection indicator in response to metallic objects passing through said coils based on said waveform exceeding said first detection threshold at a first time and exceeding said second detection threshold at a subsequent second time.

What is claimed is:

1. A medical waste collection system for detecting disposal of metallic objects into an opening of a medical waste container, the medical waste collection system comprising:
a plurality of coils including a pair of receive coils and a transmit coil spaced between the receive coils, the plurality of coils being shaped for receiving waste therethrough adjacent to the opening of the medical waste container;
a coil support frame supporting each of the coils, wherein the coil support frame comprises an outer surface and an inner surface, the inner surface defining a passage through the coil support frame for receiving the waste, and the outer surface forming grooves for receiving the plurality of coils; and a faraday shield wrapped around the coil support frame for shielding the pair of receive coils from external electrical fields.

2. The medical waste collection system of claim 1, wherein the faraday shield comprises a first faraday arrangement and a second faraday arrangement each wrapped around the coil support frame, the first faraday arrangement having first and second ends and being wrapped around the coil support frame such that the first and second ends are spaced apart from one another, and the second faraday arrangement being insulated from the first faraday arrangement and wrapped around the coil support frame such that the second faraday arrangement encompasses the spaced apart first and second ends of the first faraday arrangement.

3. The medical waste collection system of claim 2, wherein the first and second faraday arrangements each comprises a strip of non-magnetic electrically conductive material wrapped around the outer and inner surfaces of the coil support frame in an overlapping arrangement.

4. The medical waste collection system of claim 3, wherein the strip of material is selected from the group consisting of copper and aluminum.

5. The medical waste collection system of claim 2, wherein the faraday shield further comprises insulating tape wrapped around each of the spaced apart first and second ends for insulating the second faraday arrangement from the first faraday arrangement.

6. The medical waste collection system of claim 1, further comprising a field shaping arrangement wrapped around the outer surface of the coil support frame such that the field shaping arrangement encompasses the transmit coil for focusing a magnetic field generated by the transmit coil towards the passage defined by the inner surface of the coil support frame.

7. The medical waste collection system of claim 6, wherein the field shaping arrangement comprises a strip of magnetic field shaping material and a strip of insulating material each wrapped around the outer surface of the coil support frame adjacent the transmit coil.

8. The medical waste collection system of claim 6, wherein the field shaping arrangement is wrapped around the outer surface of the coil support frame such that the field shaping arrangement is disposed between and vertically spaced from the receive coils.

9. A method of making a medical waste collection system for detecting disposal of metallic objects in an opening of a medical waste container, the method comprising:
providing a coil support frame including an outer surface and in inner surface, the inner surface defining a passage through the coil support frame for receiving waste therethrough, and the outer surface forming grooves;
disposing a plurality of coils including a pair of receive coils and a transmit coil into the grooves such that the transmit coil is spaced between the pair of receive coils; and
wrapping a faraday shield around the coil support frame for shielding the pair of receiving coils from external electrical fields.

10. The method of claim 9, wherein wrapping the faraday shield around the coil support frame comprises:
wrapping a first faraday arrangement having first and second ends around the coil support frame such that the first and second ends are spaced apart from one another; and
after wrapping the first faraday arrangement, wrapping a second faraday arrangement around the coil support frame such that the second faraday arrangement is insulated from and encompasses the spaced apart first and second ends of the first faraday arrangement.

11. The method of claim 10, wherein the first and second faraday arrangements each comprises a strip of non-magnetic electrically conductive material, and further comprising:
wrapping the strip of material of the first faraday arrangement around the outer and inner surfaces of the coil support frame in an overlapping arrangement; and
after wrapping the strip of material of the first faraday arrangement, wrapping the strip of material of the second faraday arrangement around the outer and inner surfaces of the coil support frame in an overlapping arrangement such that the strip of material insulated from and encompasses the spaced apart first and second ends of the first faraday arrangement.

12. The method of claim 10, wherein wrapping the faraday shield around the coil support frame comprises, prior to wrapping the second faraday arrangement around the coil support frame, wrapping insulation tape around each of the spaced apart first and second ends of the first faraday arrangement.

13. The method of claim 9, further comprising, after wrapping the faraday shield around the coil support frame, wrapping a field shaping arrangement around the outer surface of the coil support frame such that the field shaping arrangement encompasses the transmit coil for focusing a magnetic field generated by the transmit coil towards the passage defined by the inner surface of the coil support frame.

14. The method of claim 13, wherein wrapping the field shaping arrangement around the outer surface of the coil support frame comprises wrapping a layer of insulation material and a layer of magnetic field shaping material around the outer surface of the coil support frame adjacent the transmit coil.

15. The method of claim 13, wherein wrapping the field shaping arrangement around the outer surface of the coil support frame adjacent the transmit coil comprises wrapping the field shaping arrangement around the outer surface of the coil support frame such that the field shaping arrangement is disposed between and vertically spaced from the receive coils.

16. A medical waste collection system for detecting disposal of metallic objects into an opening of a medical waste container, the medical waste collection system comprising:
a plurality of coils including a pair of receive coils and a transmit coil spaced between the receive coils, the plurality of coils being shaped for receiving waste therethrough adjacent to the opening of the medical waste container;
a coil support frame supporting each of the coils; and
a faraday shield wrapped around the coil support frame for shielding the pair of receive coils from external electrical fields,
wherein the faraday shield comprises a first faraday arrangement and a second faraday arrangement each wrapped around the coil support frame, the first faraday arrangement having first and second ends and being wrapped around the coil support frame such that the first and second ends are spaced apart from one another, and the second faraday arrangement being insulated from the first faraday arrangement and wrapped around the coil support frame such that the second faraday arrangement encompasses the spaced apart first and second ends of the first faraday arrangement.

17. The medical waste collection system of claim 16, wherein the coil support frame comprises an outer surface and an inner surface, the inner surface defining a passage through the coil support frame for receiving the waste therethrough, and the first and second faraday arrangements each comprises a strip of non-magnetic electrically conductive material wrapped around the outer and inner surfaces of the coil support frame in an overlapping arrangement.

18. The medical waste collection system of claim 16, wherein the faraday shield further comprises insulating tape wrapped around each of the spaced apart first and second ends for insulating the second faraday arrangement from the first faraday arrangement.

19. A medical waste collection system for detecting disposal of metallic objects into an opening of a medical waste container, the medical waste collection system comprising:

a plurality of coils including a pair of receive coils and a transmit coil spaced between the receive coils, the plurality of coils being shaped for receiving waste therethrough adjacent to the opening of the medical waste container;

a coil support frame supporting each of the coils; and a faraday shield wrapped around the coil support frame for shielding the pair of receive coils from external electrical fields, wherein the coil support frame comprises an outer surface and an inner surface, the inner surface defining a passage through the coil support frame for receiving the waste therethrough, and further comprising a field shaping arrangement wrapped around the outer surface of the coil support frame such that the field shaping arrangement encompasses the transmit coil for focusing a magnetic field generated by the transmit coil towards the passage defined by the inner surface of the coil support frame.

20. The medical waste collection system of claim 19, wherein the field shaping arrangement comprises a strip of magnetic field shaping material and a strip of insulating material each wrapped around the outer surface of the coil support frame adjacent the transmit coil.

* * * * *